(12) United States Patent
Knauf-Beiter et al.

(10) Patent No.: US 6,235,684 B1
(45) Date of Patent: May 22, 2001

(54) FUNGICIDAL COMBINATIONS COMPRISING PHENYLACRYLIC ACID DERIVATIVES

(75) Inventors: Gertrude Knauf-Beiter, Müllheim (DE); René Zurflüh, Basel; Bettina Gsell, Uster, both of (CH)

(73) Assignee: Novartis Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/486,519

(22) PCT Filed: Aug. 27, 1998

(86) PCT No.: PCT/EP98/05453

§ 371 Date: Feb. 28, 2000

§ 102(e) Date: Feb. 28, 2000

(87) PCT Pub. No.: WO99/11125

PCT Pub. Date: Mar. 11, 1999

(30) Foreign Application Priority Data

Aug. 29, 1997 (GB) .................................................. 9718366

(51) Int. Cl.$^7$ .......................... A01N 57/100; A01N 37/44
(52) U.S. Cl. ............................................ 504/127; 504/148
(58) Field of Search ..................... 504/127, 148

(56) References Cited

FOREIGN PATENT DOCUMENTS

| | | |
|---|---|---|
| 195 43 746 | 5/1997 | (DE) . |
| 0 610 764 | 8/1994 | (EP) . |
| 0 627 163 | 12/1994 | (EP) . |
| 0 741 970 | 11/1996 | (EP) . |
| 2 740 005 | 4/1997 | (FR) . |
| 2 742 633 | 6/1997 | (FR) . |
| WO 95/18789 | 7/1995 | (WO) . |
| WO 95/21154 | 8/1995 | (WO) . |
| WO 96/03044 | 2/1996 | (WO) . |
| WO 96/18299 | 6/1996 | (WO) . |
| WO 97/00011 | 1/1997 | (WO) . |
| WO 97/00012 | 1/1997 | (WO) . |
| WO 97/01277 | 1/1997 | (WO) . |
| WO 97/03563 | 2/1997 | (WO) . |
| WO 97/06678 | 2/1997 | (WO) . |
| WO 97/06679 | 2/1997 | (WO) . |
| WO 97/06680 | 2/1997 | (WO) . |
| WO 97/06681 | 2/1997 | (WO) . |
| WO 97/06682 | 2/1997 | (WO) . |
| WO 97/06683 | 2/1997 | (WO) . |
| WO 97/06684 | 2/1997 | (WO) . |
| WO 97/10716 | 3/1997 | (WO) . |
| WO 97/15189 | 5/1997 | (WO) . |
| WO 97/20809 | 6/1997 | (WO) . |
| WO 97/06677 | 2/1999 | (WO) . |

OTHER PUBLICATIONS

"Azoxystrobin Compositions" Research Disclosure, No. 390, Oct. 1996, pp. 673–674.
Fraine De P J et al. "A New Series of Broad–Spectrum Beta–Methoxyacrylate Funglcides with an Oxime Ether Side–Chain" Pesticide Science.

*Primary Examiner*—Allen J. Robinson
*Assistant Examiner*—Alton Pryor
(74) *Attorney, Agent, or Firm*—William A. Teoli, Jr.

(57) ABSTRACT

A method of combating phytopathogenic diseases on crop plants which comprises applying to the crop plants or the locus thereof being infested with said phytopathogenic disease an effective amount of a combination of a) a 2-(5-phenyl-3,6-diaza-2,7-dioxa-octa-3,5-dienyl) phenylacrylamide of formula I (I)

$$\text{structure with } CO-NH\cdot CH_3,\ C=N-O-CH_3,\ CH_2-O-N=C(CH_3)-C=N-O-CH_3,\ R_1,\ R_2$$

wherein $R_1$ is hydrogen, fluoro or chloro, $R_2$ is methyl, ethyl, trifluoromethyl, trifluoromethoxy, cyano, fluoro, chloro or bromo, with the proviso that $R_2$ cannot be fluoro, chloro or bromo, when $R_1$ is hydrogen;

in association with b) a broad variety of otherplant fungicides is particularly effective in combating or preventing fungal diseases of crop plants. These combinations exhibit synergistic fungicidal activity.

14 Claims, No Drawings

FUNGICIDAL COMBINATIONS COMPRISING PHENYLACRYLIC ACID DERIVATIVES

This Appln is a 371 of PCT/EP98/05453 filed Aug. 27, 1998.

The present invention relates to novel fungicidal compositions for the treatment of phytopathogenic diseases of crop plants, especially phytopathogenic fungi, and to a method of combating phytopathogenic diseases on crop plants.

It is known that certain 2-(5-phenyl-3,6-diaza-2,7-dioxa-octa-3,5-dienyl)-phenylacrylic acid derivatives have biological activity against phytopathogenic fungi, e.g. known from WO 95/18789, WO 95/21154 and WO 97/20809 where their properties and methods of preparation are described. On the other hand azole derivatives, phthalimides, phenylamides, morpholines and aminopyrimidines and numerous further compounds of different chemical classes are widely known as plant fungicides for application in various crops of cultivated plants. However, crop tolerance and activity against phytopathogenic plant fungi do not always satisfy the needs of agricultural practice in many incidents and aspects.

It has now been found that the use of a) a 2-(5-phenyl-3,6-diaza-2,7-dioxa-octa-3,5-dienyl)-phenylacrylamide of formula I

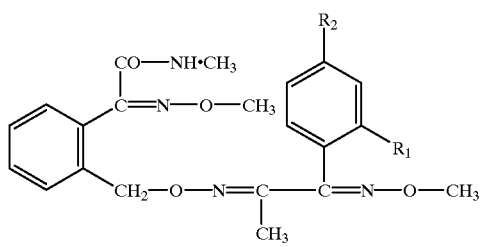

(I)

wherein $R_1$ is hydrogen, fluoro or chloro, $R_2$ is methyl, ethyl, trifluoromethyl, trifluoromethoxy, cyano, fluoro, chloro or bromo, with the proviso that $R_2$ cannot be fluoro, chloro or bromo, when $R_1$ is hydrogen;

in association with b) either an anilinopyrimidine of formula II

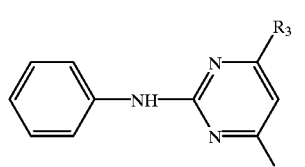

(II)

wherein $R_3$ is methyl, 1-propynyl or cyclopropyl;

or an azole of formula III

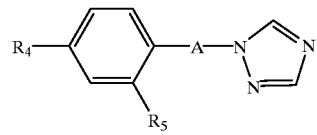

(III)

wherein

A is selected from

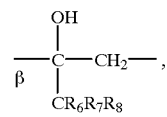

(i)

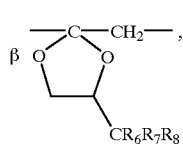

(ii)

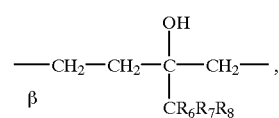

(iii)

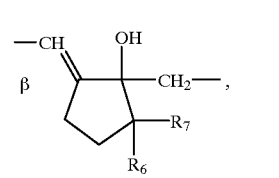

(iv)

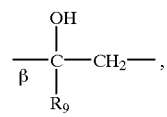

(v)

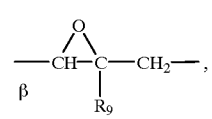

(vi)

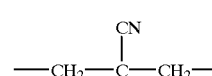

(vii)

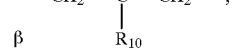

(viii)

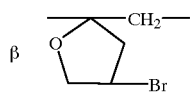

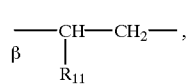

(ix)

-continued

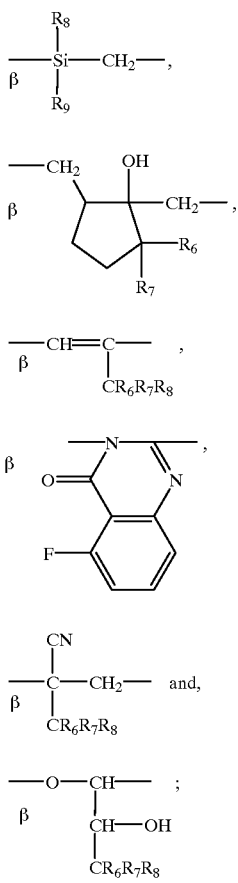

(x)

(xi)

(xii)

(xiii)

(xiv)

(xv)

whereby the β-carbon attaches to benzene ring of formula III, and wherein $R_4$ is H, F, Cl, 4-fluorophenoxy or 4-chlorophenoxy;
$R_5$ is H, Cl or F;
$R_6$ and $R_7$ are independently H or $CH_3$;
$R_8$ is $C_{1-4}$alkyl or cyclopropyl;
$R_9$ is 4-chlorophenyl or 4-fluorophenyl;
$R_{10}$ is phenyl, and
$R_{11}$ is allyloxy, $C_{1-4}$alkyl, or 1,1,2,2-tetrafluoroethoxy-methyl, and the salts of such azole fungicide;

or a morpholine fungicide of formula IV

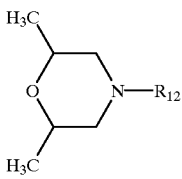

(IV)

wherein $R_{12}$ is $C_{8-15}$cycloalkyl, $C_{8-15}$alkyl, or $C_{1-4}$alkylphenyl-$C_{1-4}$alkyl, and the salts of such morpholine fungicide;

or a strobilurin compound of formula V

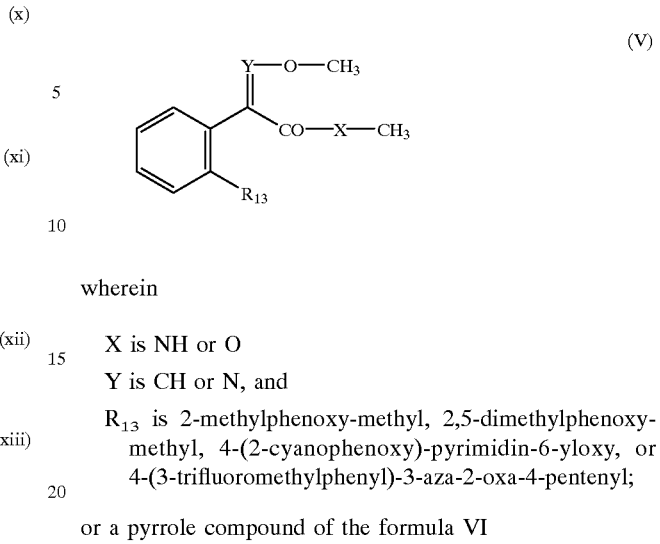

(V)

wherein

X is NH or O
Y is CH or N, and
$R_{13}$ is 2-methylphenoxy-methyl, 2,5-dimethylphenoxy-methyl, 4-(2-cyanophenoxy)-pyrimidin-6-yloxy, or 4-(3-trifluoromethylphenyl)-3-aza-2-oxa-4-pentenyl;

or a pyrrole compound of the formula VI

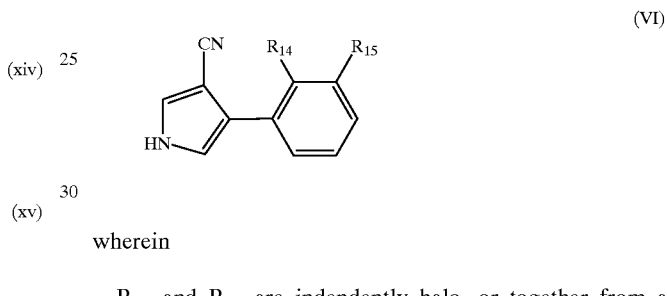

(VI)

wherein $R_{14}$ and $R_{15}$ are indendently halo, or together from a perhalomethylendioxo bridge;

or a phenylamide of the formula VII

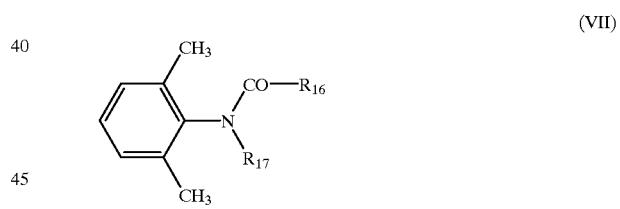

(VII)

wherein $R_{16}$ is benzyl, methoxymethyl, 2-furanyl or chloromethyl,
$R_{17}$ is 1-methoxycarbonyl-ethyl, or

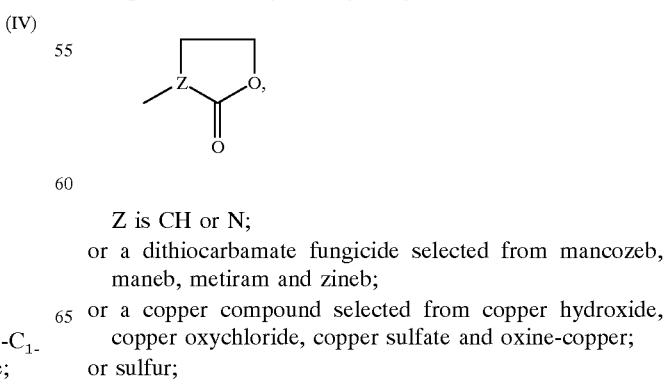

Z is CH or N;
or a dithiocarbamate fungicide selected from mancozeb, maneb, metiram and zineb;
or a copper compound selected from copper hydroxide, copper oxychloride, copper sulfate and oxine-copper;
or sulfur;

or a phthalimide compound of the formula VIII

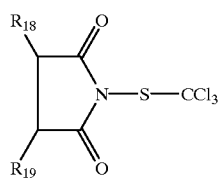
(VIII)

wherein $R_{18}$ and $R_{19}$ together form a 4-membered bridge —CH$_2$—CH=CH—CH$_2$— or =CH—CH=CH—CH=;

or with the compound of formula IX

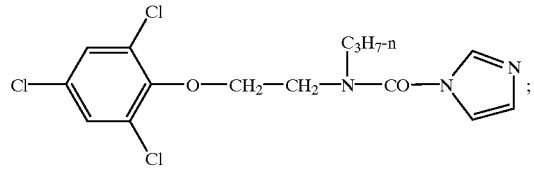
(IX)

or with the compound of formula X

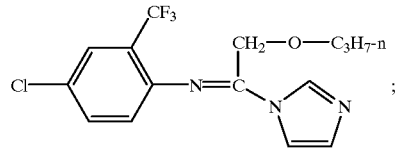
(X)

or with the compound of formula XI

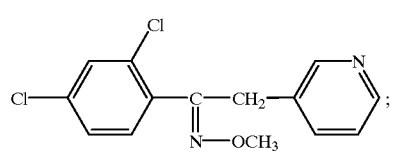
(XI)

or with the compound of formula XII

(XII)

or with the compound of formula XIII

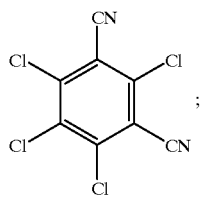
(XIII)

or with the compound of formula XIV

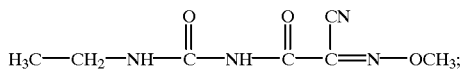
(XIV)

or with the compound of formula XV

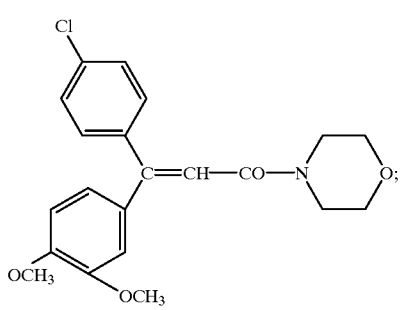
(XV)

or with the compound of formula XVI

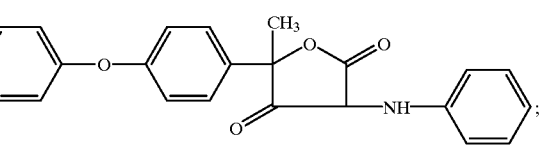
(XVI)

or with the compound of formula XVII

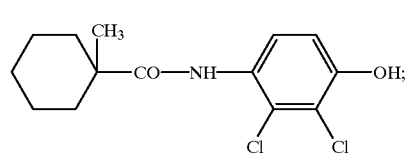
(XVII)

or with the compound of formula XVIII (XVIII)
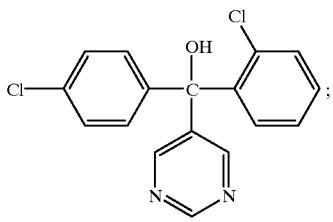

or with the compound of formula XIX (XIX)
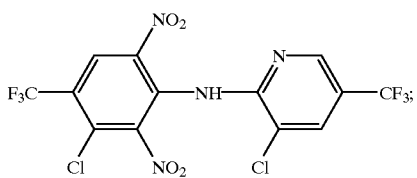

or with the compound of formula XX (XX)
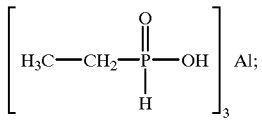

or with the compound of formula XXI (XXI)
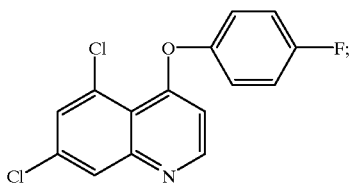

or with the compound of formula XXII (XXII)
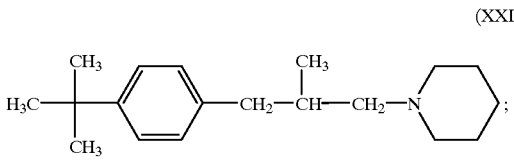

or with the compound of formula XXIII (XXIII)
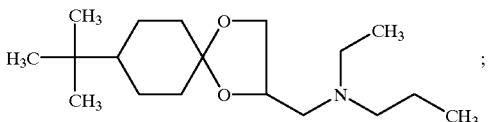

or with the compound of formula XXIV (XXIV)
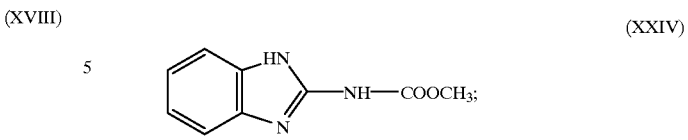

or with 2-chloro-N-(4'-fluoro-1,1'-biphenyl-2-yl) nicotinamide (compound XXV), or with 2-chloro-N-(4'-chloro-1,1'-biphenyl-2-yl) nicotinamide (compound XXVI), or with methyl N-(2-[1-(4-chlorophenyl)pyrazol-3-yloxymethyl]phenyl)-N- methoxycarbamate (compound XXVII), or with methyl N-(2-[1-(4-tolyl)pyrazol-3-yloxymethyl]phenyl)-N- methoxycarbamate (compound XXVIII), or with 2-[4-methoxy-3-(1-methylethoxy)-1,4-diazabuta-1,3-dienyloxymethyl]phenyl-2-methoximino-N-methylacetamide (compound XXIX), or with 2-[4-methoxy-3-(1-methylpropoxy)-1,4-diazabuta-1,3-dienyloxymethyl]phenyl-2-methoximino-N-methylacetamide (compound XXX), or with N-(cyclopropylmethoxy)-N'-(2-phenylacetyl)-2,3-difluoro-6-trifluoromethyl-benzamidine (compound XXXI), or with N-[3'-(1'-chloro-3-methyl 2'-oxopentan)]-3,5-dichloro-4-methylbenzamide (compound XXXII), or with methyl(2)-2-{6-[6-(trifluoromethyl)pyrid-2-yloxymethyl]-phenyl}-3-methoxyacrylate (compound XXXIII), or with 2-chloro-4-(2-fluoro-2-methylpropionylamino)-N,N-dimethylbenzamide (compound XXXIV), or with (S)-1-anilino-4-methyl-2-methylthio-4-phenylimidazolin-5-one (compound XXXV), or with N-methyl-2-{2-[α-methyl-3-(trifluoromethyl) benzyloximinomethyl]phenyl}-2-methoximinoacetamide (compound XXXVI), or with a (S)-valinamide of formula XXXVII)

(XXXVII)
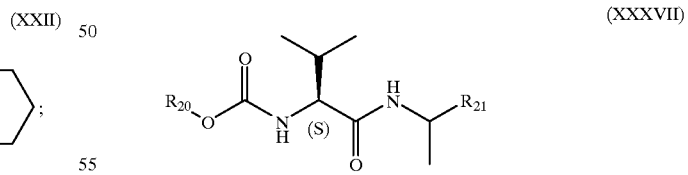

wherein $R_{20}$ is isopropyl, sec.-butyl or tert.-butyl, and $R_{21}$ is 4-chlorophenyl, 4-tolyl, 4-methoxyphenyl or β-naphthyl, preferably the compound isopropyl 2-methyl-1-[(1-p-tolylethyl)carbamoyl]-(S)-propylcarbamate (compound XXXVIIa);

or with a (S)-valinamide of formula XXXVIII

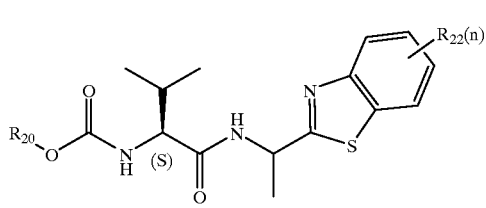

(XXXVIII)

wherein
$R_{20}$ is isopropyl, sec.-butyl or tert.-butyl,
$R_{22}$ is halogen, methyl or methoxy,
and n is 0, 1, or 2;
or with an azole of formula XXXIX

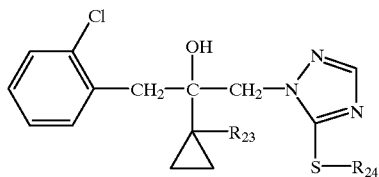

(XXXIX)

wherein
$R_{23}$ is chloro or fluoro, and
$R_{24}$ is hydrogen or methyl;
is particularly effective in combating or preventing fungal diseases of crop plants. These combinations exhibit synergistic fungicidal activity.

Among the components b) all the compounds except those of formulae XXV to XXXIX are mentioned as a particular subgroup.

Throughout this document the expression combination stands for the various combinations of components a) and b), e.g. in a single "ready-mix" form, in a combined spray mixture composed from separate formulations of the single active ingredient components, e.g. a "tank-mix", and in a combined use of the single active ingredients when applied in a sequential manner, i.e. one after the other with a reasonably short period, e.g. a few hours or days. The order of applying the components a) and b) is not essential for working the present invention.

The combinations according to the invention may also comprise more than one of the active components b), if broadening of the spectrum of disease control is desired. For instance, it may be advantageous in the agricultural practice to combine two or three components b) with the any of the compounds of formula I, or with any preferred member of the group of compounds of formula I.

From WO 95/18789, WO 95/21154 and WO 97/20809 the following specific species of formula I are known:

| Compound No. | $R_1$ | $R_2$ |
|---|---|---|
| 1.01 | H | 4-CH$_3$ |
| 1.02 | H | 4-C$_2$H$_5$ |
| 1.03 | 2-Cl | 4-Cl |
| 1.04 | H | 4-CN |

-continued

| Compound No. | $R_1$ | $R_2$ |
|---|---|---|
| 1.05 | H | 4-OCF$_3$ |
| 1.06 | 2-F | 4-CH$_3$ |
| 1.07 | 2-F | 4-F |
| 1.08 | 2-Cl | 4-F |
| 1.09 | 2-F | 4-Cl |
| 1.10 | 2-F | 4-CF$_3$ |

A preferred embodiment of the present invention is represented by those combinations which comprise as component a) a compound of the formula I wherein $R_1$ is fluoro or chloro and $R_2$ is methyl, trifluoromethyl, fluoro, chloro or bromo.

Most preferred subgroups of formula I are those wherein $R_1$ is fluoro or chloro and $R_2$ is methyl, chloro or fluoro; or wherein $R_1$ and $R_2$ are independently fluoro or chloro; or wherein $R_1$ is hydrogen, fluoro or chloro and $R_2$ is methyl, fluoro or chloro, provided that $R_2$ is methyl when $R_1$ is hydrogen.

Among the mixtures of present invention most preference is given to the mixtures of compounds 1.01, 1.03, 1.05, 1.06, 1.07, 1.08 and 1.09 with the compounds of component b), especially the commercially available products falling within the given ranges, i.e. the commercial products mentioned throughout this document. Particular preference is given to the combination of compound 1.01 with any of the components b), and to the combination of compound 1.07 with any of the components b).

Salts of the azole, amine and morpholine active ingredients are prepared by reaction with acids, e.g., hydrohalo acids such as hydrofluoric acid, hydrochloric acid, hydrobromic acid and hydroiodic acid, or sulfuric acid, phosphoric acid or nitric acid, or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzensulfonic acid, p-toluenesulfonic acid, methanesulfonic acid, salicylic acid, p-aminosalicylic acid and 1,2-naphtalenedisulfonic acid.

The active ingredient combinations are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Puccinia); Fungi imperfecti (e.g. Botrytis, Helminthosporium, Rhynchosporium, Fusarium, Septoria, Cercospora, Alternaria, Pyricularia and *Pseudocercosporella herpotrichoides*); Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). This list does not represent any limitation.

The combinations of the present invention may also be used in the area of protecting technical material against attack of fungi. Technical areas include wood, paper, leather, constructions, cooling and heating systems, ventilation and air conditioning systems, and the like. The combinations according the present invention can prevent the disadvantageous effects such as decay, discoloration or mold.

The combinations according to the present invention are particularly effective against powdery mildews and rusts, pyrenophora, rhynchosporium and leptosphaeria fungi, in particular against pathogens of monocotyledonous plants such as cereals, including wheat and barley. They are furthermore particularly effective against downy mildew species, especially against plasmopara in vine.

The amount of combination of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

Particularly preferred mixing partners of the compounds of formula II are those in which $R_3$ is methyl or cyclopropyl. These compounds are commonly known as pyrimethanil and cyprodinil.

Particularly preferred mixing partners of the compounds of formula III are those in which $R_4$ is Cl, $R_5$ and $R_6$ are H, $R_7$ is $CH_3$ and $R_8$ is cyclopropyl and A is the moiety (i) (commonly known as cyproconazole), those wherein $R_4$ and $R_5$ are Cl, $R_6$ and $R_7$ are H, $R_8$ is propyl and A is the moiety (i) (commonly known as hexaconazole); those in which $R_4$ is 4-chlorophenoxy, $R_5$ is Cl, $R_6$, $R_7$ and $R_8$ are H and A is the moiety (ii) (commonly known as difenoconazole), those in which $R_4$ and $R_5$ are Cl, $R_6$ and $R_7$ are H, $R_8$ is ethyl and A is the moiety (ii) (commonly known as etaconazole); those in which $R_4$ and $R_5$ are Cl, $R_6$ and $R_7$ are H, $R_8$ is propyl and A is the moiety (ii) (commonly known as propiconazole); those in which $R_4$ is Cl, $R_5$ is H, $R_6$, $R_7$ and $R_8$ are $CH_3$ and A is the moiety (iii) (commonly known as tebuconazole); those in which $R_4$ is Cl, $R_5$ is H and A is the moiety (iv) (commonly known as triticonazole); those in which $R_4$ is H, $R_5$ is F, $R_9$ is 4-fluorophenyl and A is the moiety (v) (commonly known as flutriafol); those in which $R_4$ is H, $R_5$ is Cl, $R_9$ is 4-fluorophenyl and A is the moiety (vi) (commonly known as epoxiconazole); those in which $R_4$ is Cl, $R_5$ is H, $R_{10}$ is phenyl and A is the moiety (vii) (commonly known as fenbuconazole), those in which $R_4$ and $R_5$ are Cl, and A is the moiety (viii) (commonly known as bromuconazole); those in which $R_4$ and $R_5$ are Cl, $R_{11}$ is propyl and A is the moiety (ix) (commonly known as penconazole); those in which $R_4$ and $R_5$ are Cl, $R_{11}$ is allyloxy and A is the moiety (ix) (commonly known as imazalil); and those in which $R_4$ and $R_5$ are Cl, $R_{11}$ is 1,1,2,2-tetrafluoroethoxymethyl and A is the moiety (ix) (commonly known as tetraconazole); those wherein $R_4$ is F, $R_5$ is H, $R_8$ is $CH_3$, $R_9$ is 4-fluorophenyl, and A is the moiety (x) (commonly known as flusilazole); those in which $R_4$ is chloro, $R_5$ is hydrogen, $R_6$ and $R_7$ are methyl and A is the moiety (xi) (commonly known as metconazole); those wherein $R_4$ and $R_5$ are chloro, $R_6$ and $R_7$ are H, $R_8$ is t-butyl and A is the moiety (xii) (commonly known as diniconazole); those wherein $R_4$ and $R_5$ are chloro and A is the moiety (xiii) (commonly known as fluquinconazole); those wherein $R_4$ is chloro, $R_5$, $R_6$ and $R_7$ are H, $R_8$ is n-butyl and A is the moiety (xiv) (commonly known as myclobutanil); and those wherein $R_4$ is chloro, $R_5$ is H, $R_6$, $R_7$ and $R_8$ are methyl and A is the moiety (xv) (commonly known as triadimenol).

Particularly preferred mixing partners of the compounds of formula IV are those wherein $R_{12}$ is cyclododecyl (commonly known as dodemorph), or $C_{10-13}$ alkyl (commonly known as tridemorph), or 3-(4-tert-butylphenyl)-2-methylpropyl (commonly known as fenpropimorph). Predominantly, the cis-positioning of the methyl groups at the morpholine ring is present in the compounds of formula IV when used in the combinations of the invention.

Particularly preferred mixing partners of the compounds of formula V are those wherein X and Y are O, and $R_{13}$ is 2-methylphenoxy-methyl (commonly known as kresoxim-methyl); or wherein X is NH, Y is N and $R_{13}$ is 2,5-dimethylphenoxy-methyl; or wherein X is O, Y is CH and $R_{13}$ is 4-(2-cyanophenoxy)-pyrimidin-6-yloxy (commonly known as azoxystrobin); or wherein X is O, Y is N and $R_{13}$ is 4-(3-trifluoromethylphenyl)-3-aza-2-oxa-4-pentenyl (compound Va; proposed common name trifloxystrobin).

Particularly preferred mixing partners of the compounds of formula VI are those wherein $R_{14}$ and $R_{15}$ are both chloro (commonly known as fenpiclonil); or wherein R14 and R15 together form a bridge —O—$CF_2$—O— (commonly known as fludioxonil).

Particularly preferred mixing partners of the compounds of formula VII are those wherein $R_{16}$ is benzyl and $R_{17}$ is 1-methoxycarbonyl-ethyl (commonly known as benalaxyl); or wherein $R_{16}$ is 2-furanyl and $R_{17}$ is 1-methoxycarbonyl-ethyl (commonly known as furalaxyl); or wherein $R_{16}$ is methoxymethyl and $R_{17}$ is 1-methoxycarbonyl-ethyl or is (R)-1-methoxycarbonyl-ethyl (commonly known as metalaxyl and R-metalaxyl); or wherein $R_{16}$ is chloromethyl and $R_{17}$ is F

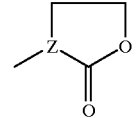

whereby Z is CH (commonly known as orfurace); or wherein $R_{16}$ is methoxymethyl and $R_{17}$ is

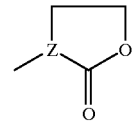

whereby Z is N (commonly known as oxadixyl).

Particularly preferred mixing partners of the compounds of formula VIII are those wherein $R_{18}$ and $R_{19}$ together form the bridge —$CH_2$—CH=CH—$CH_2$— (commonly known as captan); or wherein $R_{18}$ and $R_{19}$ together form the bridge =CH—CH=CH—CH= (commonly known as folpet).

The compound of formula IX is commonly known as prochloraz.

The compound of formula X is commonly known as triflumizole.

The compound of formula XI is commonly known as pyrifenox.

The compound of formula XII is commonly known as acibenzolar-S-methyl.

The compound of formula XIII is commonly known as chlorothalonil.

The compound of formula XIV is commonly known as cymoxanil.

The compound of formula XV is commonly known as dimethomorph.

The compound of formula XVI is commonly known as famoxadone.

The compound of formula XVII is commonly known as fenhexamide.

The compound of formula XVIII is commonly known as fenarimol.

The compound of formula XIX is commonly known as fluazinam.

The compound of formula XX is commonly known as fosetyl-aluminium.

The compound of formula XXI is commonly known as quinoxyfen.

The compound of formula XXII is commonly known as fenpropidine.

The compound of formula XXIII is commonly known as spiroxamine.

The compound of formula XXIV is commonly known as carbendazime.

The compound of formula XXXV is commonly known as fenamidone.

The compound of formula XXXVIIa is commonly known as iprovalicarb (proposed common name).

The specific compounds b) mentioned in the preceding paragraphs are commercially available. Other compounds falling under the scope of the various groups of component b) are obtainable according to procedures analogous to those known for preparing the commercially available compounds.

It has been found that the use of compounds of formulae II to XXXVII in combination with the compound of formula I surprisingly and substantially enhance the effectiveness of the latter against fungi, and vice versa. Additionally, the method of the invention is effective against a wider spectrum of such fungi that can be combated with the active ingredients of this method, when used solely.

Specific preferred mixtures according to the present invention are understood to be represented by the combinations of active ingredients of formula I, or any of the subgroups of formula I, or specifically mentioned members of the subgroups with a second fungicide selected from the group comprising pyrimethanil, cyprodinil, cyproconazole, hexaconazole; difenoconazole, etaconazole, propiconazole, tebuconazole, triticonazole, flutriafol, epoxiconazole, fenbuconazole, bromuconazole, penconazole, imazalil, tetraconazole, flusilazole, metconazole, diniconazole, fluquinconazole, myclobutanil, triadimenol, dodemorph, tridemorph, fenpropimorph, mancozeb, maneb, metiram, zineb, copper hydroxide, copper oxychloride, copper sulfate, oxine-copper, sulfur, kresoxim-methyl, azoxystrobin, 2-[2-(2,5-dimethylphenoxy-methyl)-phenyl]-2-methoximino-acetic acid N-methyl-amide, methyl 2-{2-[4-(3-trifluoromethylphenyl)-3-aza-2-oxa-4-pentenyl]-phenyl}-2-methoxyimino-acetate, fenpiclonil, fludioxonil, benalaxyl, furalaxyl, metalaxyl, R-metalaxyl, orfurace, oxadixyl, captan, folpet, prochloraz, triflumizole, pyrifenox, acibenzolar-S-methyl, chlorothalonil, cymoxanil, dimethomorph, famoxadone, fenhexamide, fenarimol, fluazinam, fosetyl-aluminium, quinoxyfen, fenpropidine, spiroxamine, and carbendazime. Further preferred as second fungicide of component b) are fenamidone and iprovalicarb.

From this group a subgroup b1 is preferred comprising combinations with cyproconazole, hexaconazole; difenoconazole, propiconazole, tebuconazole, flutriafol, epoxiconazole, fenbuconazole, bromuconazole, penconazole, tetraconazole, flusilazole, metconazole, diniconazole, triadimenol, fluquinconazole and prochloraz.

From this group combinations with propiconazole, difenoconazole, penconazole, tebuconazole, prochloraz, epoxiconazole and cyproconazole are of particular interest as preferred embodiments of this invention as subgroup b1a.

A further preferred subgroup b2 comprises combinations with comprising cyprodinil, tridemorph, fenpropimorph, kresoxim-methyl, azoxystrobin, methyl 2-{2-[4-(3-trifluoromethylphenyl)-3-aza-2-oxa4-pentenyl]-phenyl}-2-methoxyimino-acetate, acibenzolar-S-methyl, chlorothalonil, famoxadone, quinoxyfen, fenpropidine and carbendazime.

From this group combinations with cyprodinil, fenpropimorph, kresoxim-methyl, azoxystrobin, methyl 2-{2-[4-(3-trifluoromethylphenyl)-3-aza-2-oxa4-pentenyl]-phenyl}-2-methoxyimino-acetate, acibenzolar-S-methyl and fenpropidine are of particular interest as preferred embodiments of this invention as subgroup b2a.

Further groups of interest are the following combinations:

compound I.01 with groups b1 and b2, or with groups b1a and b2a;

compound I.03 with groups b1 and b2, or with groups b1a and b2a;

compound I.05 with groups b1 and b2, or with groups b1a and b2a;

compound I.06 with groups b1 and b2, or with groups b1a and b2a;

compound I.07 with groups b1 and b2, or with groups b1a and b2a;

compound I.08 with groups b1 and b2, or with groups b1a and b2a;

compound I.09 with groups b1 and b2, or with groups b1a and b2a.

The weight ratio of a):b) is so selected as to give a synergistic fungicidal action. In general the weight ratio of a):b) is between 10:1 and 1:400. The synergistic action of the composition is apparent from the fact that the fungicidal action of the composition of a)+b) is greater than the sum of the fungicidal actions of a) and b).

Where the component b) is an anilinopyrimidine of formula II the weight ratio of a):b) is for example between 1:2 and 1:36, especially 1:2 and 1:18, and more preferably 1:3 and 1:8.

Where the component b) is an azole fungicide of formula III the weight ratio of a):b) is for example between 10:1 and 1:20, especially 5:1 and 1:10, and more preferably 2:1 and 1:4.

Where component b) is a morpholine fungicide of formula IV, the weight ratio of a):b) is for example between 1:2 and 1:30, especially 1:3 and 1:15, and more preferably 1:3 and 1:10.

Where component b) is a strobilurin fungicide of formula V, the weight ratio of a):b) is for example between 5:1 and 1:10, especially 3:1 and 1:3, and more preferably 1:2 and 1:5.

Where component b) is a pyrrole fungicide of formula VI, the weight ratio of a):b) is for example between 1:3 and 1:30, especially 1:1.5 and 1:7, and more preferably 1:2 and 1:5.

Where component b) is a phenylamide fungicide of formula VII, the weight ratio of a):b) is for example between 3:1 and 1:12, especially 2.5:1 and 1:6,. and more preferably 2:1 to 1:3.

Where component b) is a dithiocarbamte fungicide, the weight ratio of a):b) is for example between 1:3 and 1:120, especially 1:4 and 1:60, and more preferably 1:7 and 1:25.

Where component b) is a copper compound fungicide, the weight ratio of a):b) is for example between 1:1.5 and 1:100, especially 1:2 and 1:50, and more preferably 1:5 and 1:30.

Where component b) is a sulfur fungicide, the weight ratio of a):b) is for example between 1:6 and 1:400, especially 1:8 and 1:200, and more preferably 1:10 and 1:100.

Where component b) is a phthalimide fungicide of formula VIII, the weight ratio of a):b) is for example between 1:3 and 1:80, especially 1:4 and 1:40, and more preferably 1:8 and 1:20.

Where component b) is the compound of formula IX, the weight ratio of a):b) is for example between 1:2 and 1:25, especially 1:4 and 1:12, and more preferably 1:5 and 1:8.

Where component b) is the compound of formula X, the weight ratio of a):b) is for example between 3:1 and 1:16, especially 2.5:1 and 1:8, and more preferably 1:1 and 1:4.

Where component b) is the compound of formula XI, the weight ratio of a):b) is for example between 8:1 and 1:4, especially 2.5:1 and 1:2, and more preferably 2:1 and 1:1.

Where component b) is the compound of formula XII, the weight ratio of a):b) is for example between 6:1 and 1:2, especially 6:1 and 2:1, and more preferably 5:1 and 2:1.

Where component b) is the compound of formula XIII, the weight ratio of a):b) is for example between 1:3 and 1:40, especially 1:4 and 1:20, and more preferably 1:5 and 1:10.

Where component b) is the compound of formula XIV, the weight ratio of a):b) is for example between 3:1 and 1:8, especially 2.5:1 and 1:4, and more preferably 2:1 and 1:2.

Where component b) is the compound of formula XV, the weight ratio of a):b) is for example between 1.5:1 and 1:12, especially 1:1 and 1:6, and more preferably 1:1 and 1:4.

Where component b) is the compound of formula XVI, the weight ratio of a):b) is for example between 1.5:1 and 1:10, especially 1:1 and 1:5, and more preferably 1:1 and 1:3.

Where component b) is the compound of formula XVII, the weight ratio of a):b) is for example between 2:1 and 1:30, especially 1.5:1 and 1:15, and more preferably 1:1 and 1:5.

Where component b) is the compound of formula XVIII, the weight ratio of a):b) is for example between 8:1 and 1:4, especially 2.5:1 and 1:2, and more preferably 2:1 and 1:1.

Where component b) is the compound of formula XIX, the weight ratio of a):b) is for example between 1.5:1 and 1:12, especially 1:1 and 1:6, and more preferably 1:1 and 1:4.

Where component b) is the compound of formula XX, the weight ratio of a):b) is for example between 1:3 and 1:80, especially 1:4 and 1:40 and more preferably 1:1 and 1:25.

Where component b) is the compound of formula XXI, the weight ratio of a):b) is for example between 2:1 and 1:5, especially 1.5:1 and 1:2.5, and more preferably 1:1 and 1:2.

Where component b) is the compound of formula XXII, the weight ratio of a):b) is for example between 1:2 and 1:30, especially 1:3 and 1:15, and more preferably 1:3 and 1:10.

Where component b) is the compound of formula XXIII, the weight ratio of a):b) is for example between 1:2.5 and 1:30, especially 1:3 and 1:15, and more preferably 1:3 and 1:10.

Where component b) is the compound of formula XXIV, the weight ratio of a):b) is for example between 1.5:1 and 1:10, especially 1:1 and 1:5, and more preferably 1:2 and 1:4.

Where component b) is the compound of formula XXV, the weight ratio of a):b) is for example between 5:1 and 1:20, especially 2:1 and 1:20, and more preferably 1:1. and 1:10.

Where component b) is the compound of formula XXVI, the weight ratio of a):b) is for example between 5:1 and 1:20, especially 2:1 and 1:20, and more preferably 1:1 and 1:10.

Where component b) is the compound of formula XXVII, the weight ratio of a):b) is for example between 5:1 and 1:5, especially 3:1 and 1:3, and more preferably 2:1 and 1:2.

Where component b) is the compound of formula XXVIII, the weight ratio of a):b) is for example between 5:1 and 1:5, especially 3:1 and 1:3, and more preferably 2:1 and 1:2.

Where component b) is the compound of formula XXIX, the weight ratio of a):b) is for example between 5:1 and 1:5, especially 3:1 and 1:3, and more preferably 2:1 and 1:2.

Where component b) is the compound of formula XXX, the weight ratio of a):b) is for example between 5:1 and 1:5, especially 3:1 and 1:3, and more preferably 2:1 and 1:2.

Where component b) is the compound of formula XXXI, the weight ratio of a):b) is for example between 5:1 and 1:20, especially 2:1 and 1:10, and more preferably 1:1 and 1:5.

Where component b) is the compound of formula XXXII, the weight ratio of a):b) is for example between 5:1 and 1:5, especially 2:1 and 1:2, and more preferably 1.5:1 and 1:1.5.

Where component b) is the compound of formula XXXIII, the weight ratio of a):b) is for example between 5:1 and 1:5, especially 3:1 and 1:3, and more preferably 2:1 and 1:2.

Where component b) is the compound of formula XXXIV, the weight ratio of a):b) is for example between 5:1 and 1:20, especially 3:1 and 1:10, and more preferably 2:1 and 1:5.

Where component b) is the compound of formula XXXV, the weight ratio of a):b) is for example between 6:1 and 1:6, especially 2:1 and 1:5, and more preferably 2:1 and 1:2.

Where component b) is the compound of formula XXXVI, the weight ratio of a):b) is for example between 5:1 and 1:5, especially 3:1 and 1:3 and more preferably 2:1. and 1:2.

Where component b) is a compound of formula XXXVII, the weight ratio of a):b) is for example between 5:1 and 1:5, especially 3:1 and 1:3 and more preferably 2:1. and 1:2.

Where component b) is a compound of formula XXXVIII, the weight ratio of a):b) is for example between 5:1 and 1:5, especially 3:1 and 1:3 and more preferably 2:1. and 1:2.

Where component b) is a compound of formula XXXIX, the weight ratio of a):b) is for example between 10:1 and 1:20, especially 5:1 and 1:10 and more preferably 2:1. and 1:4.

The method of the invention comprises applying to the treated plants or the locus thereof in admixture or separately, a fungicidally effective aggregate amount of a compound of formula I and a compound of component b).

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, germinated or soaked seeds.

The novel combinations are extremely effective on a broad spectrum of phytopathogenic fungi, in particular from the Ascomycetes and Basidiomycetes classes. Some of them have a systemic action and can be used as foliar and soil fungicides.

The fungicidal combinations are of particular interest for controlling a large number of fungi in various crops or their seeds, especially wheat, rye, barley, oats, rice, maize, lawns, cotton, soybeans, coffee, sugarcane, fruit and ornamentals in horticulture and viticulture, in vegetables such as cucumbers, beans and cucurbits, and in field crops such as potatoes, tobacco and sugarbeets.

The combinations are applied by treating the fungi or the seeds, plants or materials threatened by fungus attack, or the soil with a fungicidally effective amount of the active ingredients.

The agents may be applied before or after infection of the materials, plants or seeds by the fungi.

The novel combinations are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

Puccinia species in cereals,

Rhizoctonia species in cotton, rice and lawns,

Ustilago species in cereals and sugarcane,

*Venturia inaequalis* (scab) in apples,

Helminthosporium species in cereals,

*Septoria nodorum* in wheat,

*Septoria tritici* in wheat wheat,

*Rhynchosporium secalis* on barley,

*Botrytis cinerea* (gray mold) in strawberries, tomatoes and grapes,

*Cercospora arachidicola* in groundnuts,

*Peronospora tabacina* in tobacco,

*Pseudocercosporella herpotrichoides* in wheat and barley,

*Pyrenophera teres* in barley,

*Pyricularia oryzae* in rice,

*Phytophthora infestans* in potatoes and tomatoes,

Fusarium and Verticillium species in various plants,

*Plasmopara viticola* in grapes,

Alternaria species in fruit and vegetables.

When applied to the plants the compound of formula I is applied at a rate of 25 to 150 g/ha, particularly 50 to 125 g/ha, e.g. 75, 100, or 125 g/ha, in association with 20 to 3000 g/ha, particularly 20 to 2000 g/ha, e.g. 20. g/ha, 30 g/ha, 40 g/ha, 75 g/ha, 80 g/ha, 100 g/ha, 125 g/ha, 150 g/ha, 175 g/ha, 200 g/ha, 300 g/ha, 500 g/ha, 1000 g/ha, 1200 g/ha, 1500 g/ha, 2000 g/ha, or in some cases like sulfur up to 10000 g/ha of a compound of component b), depending on the class of chemical employed as component b).

Where the component b) is an anilinopyrimidine of formula II for example 300 to 900 g a.i./ha is applied in association with the compound of formula I. Where the component b) is an azole fungicide of formula III for example 20 to 350 g a.i./ha is applied in association with the compound of formula I. Where the component b) is an morpholine of formula IV for example 300 to 750 g a.i./ha is applied in association with the compound of formula I. Where the component b) is a strobilurin of formula V for example 75 to 250 g a.i./ha is applied in association with the compound of formula I. Where the component b) is a pyrrole of formula VI for example 200 to 750 g a.i./ha is applied in association with the compound of formula I. Where the component b) is a phenylamide of formula VII for example 50 to 300 g a.i./ha is applied in association with the compound of formula I. Where the component b) is a dithiocarbamate for example 500 to 3000 g a.i./ha is applied in association with the compound of formula I. Where the component b) is a copper compound for example 250 to 2500 g a.i. is applied in association with the compound of formula I. Where the component b) is sulfur for example 1000 to 10000 g a.i. is applied in association with the compound of formula I. Where the component b) is a phthalimide of formula VIII for example 500 to 2000 g a.i./ha is applied in association with the compound of formula I. Where the component b) is the compound of formula IX for example 400 to 600 g a.i./ha is applied in association with the compound of formula I. Where the component b) is the compound of formula X for example 50 to 400 g a.i./ha is applied in association with the compound of formula I. Where the component b) is the compound of formula XI for example 20 to 100 g a.i./ha is applied in association with the compound of formula I. Where the component b) is the compound of formula XII for example 20 to 40 g a.i./ha is applied in association with the compound of formula I. Where the component b) is the compound of formula XIII for example 500 to 1000 g a.i./ha is applied in association with the compound of formula I. Where the component b) is the compound of formula XIV for example 50 to 200 g a.i./ha is applied in association with the compound of formula I. Where the component b) is the compound of formula XV for example 100 to 300 g a.i./ha is applied in association with the compound of formula I. Where the component b) is the compound of formula XVI for example 125 to 250 g a.i./ha is applied in association with the compound of formula I. Where the component b) is the compound of formula XVII for example 100 to 750 g a.i./ha is applied in association with the compound of formula I. Where the component b) is the compound of formula XVIII for example 20 to 100 g a.i./ha is applied in association with the compound of formula I. Where the component b) is the compound of formula XIX for example 100 to 300 g a.i./ha is applied in association with the compound of formula I. Where the component b) is the compound of formula XX for example 500 to 2000 g a.i./ha is applied in association with the compound of formula I. Where the component b) is the compound of formula XXI for example 75 to 125 g a.i./ha is applied in association with the compound of formula I. Where the component b) is the compound of formula XXII for example 300 to 750 g a.i./ha is applied in association with the compound of formula I. Where the component b) is the compound of formula XXIII for example 375 to 750 g a.i./ha is applied in association with the compound of formula I. Where the component b) is the compound of formula XXIV for example 125 to 250 g a.i./ha is applied in association with the compound of formula I. Where the component b) is the compound of formula XXV for example 50 to 2000 g a.i./ha is applied in association with the compound of formula I. Where the component b) is the compound of formula XXVI for example 50 to 2000 g a.i./ha is applied in association with the compound of formula I. Where the component b) is the compound of formula XXVII for example 50 to 300 g a.i./ha is applied in association with the compound of formula I. Where the component b) is the compound of formula XXVIII for example 50 to 300 g a.i./ha is applied in association with the compound of formula I. Where the component b) is the compound of formula XXIX for example 50 to 300 g a.i./ha is applied in association with the compound of formula I. Where the component b) is the compound of formula XXX for example 50 to 300 g a.i./ha is applied in association with the compound of formula I. Where the component b) is the compound of formula XXXI for example 100 to 1000 g a.i./ha is applied in association with the compound of formula I. Where the component b) is the compound of formula XXXII for example 50 to 200 g a.i./ha is applied in association with the compound of formula I. Where the component b) is the compound of formula XXXIII for example 50 to 300 g a.i./ha is applied in association with the compound of formula I. Where the component b) is the compound of formula XXXIV for example 20 to 2000 g a.i./ha is applied in association with the compound of formula I. Where the component b) is the compound of formula XXXV for example 50 to 400 g a.i./ha is applied in association with the compound of formula I. Where the component b) is the compound of formula XXXVI for example 50 to 300 g a.i./ha is applied in association with the compound of formula I. Where the component b) is a compound of formula XXXVII for example 50 to 400 g a.i./ha is applied in association with the compound of formula I. Where the component b) is a compound of formula XXXVIII for example 50 to 400 g a.i./ha is applied in association with the compound of formula I. Where the component b) is a compound of formula XXXIX for example 20 to 350 g a.i./ha is applied in association with the compound of formula I.

In agricultural practice the application rates of the combination depend on the type of effect desired, and range from 0.02 to 4 kg of active ingredient per hectare.

When the active ingredients are used for treating seed, rates of 0.001 to 50 g a.i. per kg, and preferably from 0.01 to 10 g per kg of seed are generally sufficient.

The invention also provides fungicidal compositions comprising a compound of formula I and a compound of component b).

The composition of the invention may be employed in any conventional form, for example in the form of a twin pack, an instant granulate, a flowable formulation, an emulsion concentrate or a wettable powder in combination with agriculturally acceptable adjuvants. Such compositions may be produced in conventional manner, e.g. by mixing the active ingredients with appropriate adjuvants (diluents or solvents and optionally other formulating ingredients such as surfactants). Also conventional slow release formulations may be employed where long lasting efficacy is intended.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least the compound of formula I together with a compound of component b), and optionally other active agents, particularly microbides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ dilute formulations.

The Examples which follow serve to illustrate the invention, "active ingredient" denoting a mixture of compound I and a compound of component b) in a specific mixing ratio.

FORMULATION EXAMPLES

| Wettable powders | a) | b) | c) |
|---|---|---|---|
| active ingredient [I:comp b) = 1:3(a), 1:2(b), 1:1(c)] | 25% | 50% | 10% |
| sodium lignosulfonate | 5% | 5% | — |
| sodium lauryl sulfate | 3% | — | 5% |
| sodium diisobutylnaphthalenesulfonate | —6 | 10 | |
| phenol polyethylene glycol ether (7–8 mols of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:comp b) = 1:6) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient [I:comp b) = 1:6(a), 1:2(b), 1:10(c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredient (I:comp b) = 2:1) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
| --- | --- |
| active ingredient (I:comp b) = 1:10) | 8% |
| polyethylene glycol (mol. wt. 200) | 3% |
| kaolin | 89% |

The finely ground active ingredient is uniformly applied, in a mixer, to the kaolin moistened with polyethylene glycol. Non-dusty coated granules are obtained in this manner.

| Suspension concentrate | |
| --- | --- |
| active ingredient (I:comp b) = 1:8) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula I and a compound of component b), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8–15 microns.

The resulting formulation is applied to seeds as an aqueous suspension in an apparatus suitable for that purpose.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20–22; 1967):

ppm=milligrams of active ingredient (=a.i.) per liter of spray mixture

X=% action by active ingredient I using p ppm of active ingredient

Y=% action by active ingredient II using q ppm of active ingredient.

According to COLBY, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

Alternatively the synergistic action may also be determined from the dose response curves according to the so-called WADLEY method. With this method the efficacy of the a.i. is determined by comparing the degree of fungal attack on treated plants with that on untreated, similarly inoculated and incubated check plants. Each a.i. is tested at 4 to 5 concentrations. The dose response curves are used to establish the EC90 (i.e. concentration of a.i. providing 90% disease control) of the single compounds as well as of the combinations (EC $90_{observed}$). The thus experimentally found values of the mixtures at a given weight ratio are compared with the values that would have been found were only a complementary efficacy of the components was present (EC 90 $(A+B)_{expected}$). The EC 90 $(A+B)_{expected}$ is calculated according to Wadley (Levi et al., EPPO- Bulletin 16, 1986, 651–657):

$$EC\,90(A+B)_{expected} = \frac{a+b}{\frac{a}{EC90\,(A)_{observed}} + \frac{b}{EC90\,(B)_{observed}}}$$

wherein a and b are the weight ratios of the compounds A and B in the mixture and the indexes (A), (B), (A+B) refer to the observed EC 90 values of the compounds A, B or the given combination A+B thereof. The ratio EC90 $(A+B)_{expected}$/EC90 $(A+B)_{observed}$ expresses the factor of interaction (F). In case of synergism, F is >1.

EXAMPLE B-1

Action against *Botrytis cinerea* on apple fruits

Artificially damaged apples are treated by dropping a spray mixture of the active ingredient mixture onto the damage sites. The treated fruits are inoculated two hours later with a spore suspension of the fungus and incubated for six days at high humidity and 18° C. The fungicidal action of the test compound is derived from the radial growth of the fungus on treated fruits relative to untreated fruits.

EXAMPLE B-2

Efficacy against *Erysiphe graminis* f.sp. *tritici* on wheat a) Protective Treatment:

Fifteen wheat seeds c.v. "Arina" are sown in plastic pots of 50 ml and grown for 7 to 12 days at 22/19° C., 50–70% rH in the greenhouse. When the primary leaves have fully expanded, the plants are spray treated with aqueous spray liquids containing the single compounds, or mixtures thereof (hereinafter a.i.). All compounds are used as experimental or commercially available formulations, combinations are applied as tank mixtures. The application comprises foliar spraying to near runoff (three pots per treatment). 7 days after the application, the plants are inoculated in a settling tower with fresh spores of *Erysiphe graminis* f. sp. *tritici* by dusting the conidia on the test plants The plants are then incubated in a growth chamber at 20° C., 60% rH. Six days after inoculation, the percentage of infection on primary leaves is evaluated. The efficacy of the a.i. is determined by comparing the degree of fungal attack on treated plants with that on untreated, similarly inoculated and incubated check plants. Each a.i. is tested at 3 to 5 concentrations. The results are evaluated according to the COLBY method.

Results:

aa) Mixtures of Compound 1.07 with Cyproconazole, *E. graminis*, protective

| Comp. 1.07 (mg a.i./l) | Cyproconazole (mg a.i./l) | Mixing ratio | % activity observed | % activity expected |
|---|---|---|---|---|
| 0.0025 | | | 2 | |
| 0.005 | | | 2 | |
| 0.01 | | | 3 | |
| 0.025 | | | 20 | |
| | 0.01 | | 3 | |
| | 0.025 | | 5 | |
| | 0.05 | | 7 | |
| | 0.1 | | 12 | |
| 0.0025 | 0.01 | 1:4 | 17 | 6 |
| | 0.025 | 1:10 | 20 | 7 |
| 0.005 | 0.01 | 1:2 | 23 | 6 |
| | 0.025 | 1:5 | 38 | 7 |
| | 0.05 | 1:10 | 42 | 9 |
| 0.01 | 0.01 | 1:1 | 17 | 6 |
| | 0.05 | 1:5 | 15 | 10 |
| 0.025 | 0.025 | 1:1 | 23 | 24 |
| | 0.05 | 1:2 | 42 | 26 |
| | 0.1 | 1:4 | 40 | 30 | ab) Mixtures of Compound 1.07 with Propiconazole, *E. graminis.* protective

| Comp. 1.07 (mg a.i./l) | Propiconazole (mg a.i./l) | Mixing ratio | % activity observed | % activity expected |
|---|---|---|---|---|
| 0.01 | | | 0 | |
| 0.025 | | | 3 | |
| 0.05 | | | 4 | |
| 0.1 | | | 7 | |
| 0.25 | | | 10 | |
| | 0.025 | | 2 | |
| | 0.05 | | 6 | |
| | 0.1 | | 7 | |
| | 0.25 | | 11 | |
| | 0.5 | | 24 | |
| 0.01 | 0.01 | 1:1 | 6 | 0 |
| | 0.05 | 1:5 | 20 | 6 |
| | 0.1 | 1:10 | 27 | 7 |
| 0.025 | 0.025 | 1:1 | 10 | 5 |
| | 0.05 | 1:2 | 21 | 9 |
| | 0.1 | 1:4 | 33 | 10 |
| | 0.25 | 1:10 | 38 | 14 |
| 0.05 | 0.01 | 5:1 | 30 | 4 |
| | 0.025 | 2:1 | 25 | 6 |
| | 0.05 | 1:1 | 29 | 10 |
| | 0.1 | 1:2 | 30 | 11 |
| | 0.25 | 1:5 | 37 | 15 |
| | 0.5 | 1:10 | 42 | 27 |
| 0.1 | 0.025 | 4:1 | 23 | 9 |
| | 0.05 | 2:1 | 33 | 13 |
| | 0.1 | 1:1 | 34 | 14 |
| | 0.5 | 1:5 | 34 | 29 |
| | 1 | 1:10 | 44 | 39 |
| 0.25 | 0.05 | 5:1 | 40 | 15 |
| | 0.25 | 1:1 | 38 | 20 |
| | 0.5 | 1:2 | 44 | 32 |
| | 1 | 1:4 | 42 | 41 | b) Curative Treatment:

Wheat plants cv. Arina are grown in standard soil in 50 ml pots (approx. 15 plants per pot) in the greenhouse at 22/19° C. and 14 hours light per day. At test begin the plants are 8 days old. For inoculation, conidia are dusted over the test plants and the plants are incubated at 18–20° C. until treatment. The fungicide treatment is carried out 3 days after inoculation by spraying the test plants with diluted spray suspensions of the individual active ingredients or mixtures, being prepared by suspension in demineralized water and appropriate dilution.

12 plants in 3 pots are used for each treatment. 3 to 4 days after treatment the tests are evaluated by estimating the percentage of fungal attack on the leaves. The activity is calculated relative to the disease on the check plants. The fungicide interactions in the mixtures are calculated according to the COLBY method.

Results:

ba) Mixtures of Compound 1.07 with Cyprodinil, *E. graminis*, curative

| Comp. 1.07 (mg a.i./l) | Cyprodinil (mg a.i./l) | Mixing ratio | % activity observed | % activity expected |
|---|---|---|---|---|
| 0.25 | | | 43 | |
| 0.5 | | | 47 | |
| 1 | | | 54 | |
| | 0.25 | | 0 | |
| | 0.5 | | 0 | |
| | 2.5 | | 0 | |
| | 5 | | 0 | |
| | 10 | | 0 | |
| 0.25 | 0.25 | 1:1 | 64 | 43 |
| | 0.5 | 1:2 | 51 | 43 |
| | 2.5 | 1:10 | 63 | 44 |
| 0.5 | 0.5 | 1:1 | 58 | 47 |
| | 5 | 1:10 | 76 | 47 |
| 1 | 5 | 1:5 | 64 | 54 |
| | 10 | 1:10 | 70 | 54 | bb) Mixtures of Compound 1.07 with Cyproconazole, *E. graminis*, curative

| Comp. 1.07 (mg a.i./l) | Cyproconazole (mg a.i./l) | Mixing ratio | % activity observed | % activity expected |
|---|---|---|---|---|
| 0.0025 | | | 1 | |
| 0.005 | | | 6 | |
| 0.01 | | | 7 | |
| 0.025 | | | 10 | |
| | 0.025 | | 5 | |
| | 0.05 | | 6 | |
| | 0.1 | | 18 | |
| 0.0025 | 0.025 | 1:10 | 16 | 6 |
| 0.005 | 0.025 | 1:5 | 13 | 11 |
| | 0.05 | 1:10 | 24 | 12 |
| 0.01 | 0.01 | 1:1 | 20 | 11 |
| | 0.05 | 1:5 | 21 | 13 |
| 0.025 | 0.025 | 1:1 | 27 | 15 |
| | 0.05 | 1:2 | 24 | 15 |
| | 0.1 | 1:4 | 28 | 26 | bc) Mixtures of Compound 1.07 with Fenpropidin, *E. graminis*, curative (2 days)

| Comp 1.07 (mg a.i./l) | Fenpropidin (mg a.i./l) | Mixing ratio | % activity observed | % activity expected |
|---|---|---|---|---|
| 0.5 | | | 41 | |
| 1 | | | 52 | |
| 2.5 | | | 72 | |
| | 0.5 | | 8 | |
| | 1 | | 8 | |
| | 2.5 | | 13 | |

-continued

| Comp 1.07 (mg a.i./l) | Fenpropidin (mg a.i./l) | Mixing ratio | % activity observed | % activity expected |
|---|---|---|---|---|
| | 5 | | 27 | |
| | 10 | | 41 | |
| 0.5 | 0.5 | 1:1 | 59 | 46 |
| | 1 | 1:2 | 61 | 46 |
| | 2.5 | 1:5 | 61 | 49 |
| | 5 | 1:10 | 68 | 57 |
| 1 | 1 | 1:1 | 87 | 56 |
| | 5 | 1:5 | 83 | 65 |
| | 10 | 1:10 | 83 | 71 |
| 2.5 | 2.5 | 1:1 | 89 | 76 |
| | 5 | 1:2 | 90 | 80 |
| | 10 | 1:4 | 96 | 83 |
| 5 | 5 | 1:1 | 95 | 90 |
| | 10 | 1:2 | 95 | 90 |

EXAMPLE B-3

Activity against *Uncinula necator*

Grape plants in the 4–6 leaf stage, variety Gutedel, are inoculated with conidia of *Uncinula necator* by dusting the conidia over the test plants. After 2 days under high humidity and reduced light intensity, the plants are incubated for 10–14 days in a growth chamber at 70% rH and 22° C. 3 days after inoculation the active ingredients and the mixtures are applied by spraying aqueous suspensions being prepared by suspending the a.i.s in demineralized water and appropriate dilution. 5 plants are used for every treatment. 12 days after inoculation the tests are evaluated by estimating the percentage of fungal leaf attack relative to the disease on the check plants. The fungicide interactions in the mixtures are calculated according to COLBY method.

Results:

Mixtures of Compound 1.07 with Penconazole, *U. necator*, curative

| Comp. 1.07 (mg a.i./l) | Penconazole (mg a.i./l) | Mixing ratio | % activity observed | % activity expected |
|---|---|---|---|---|
| 0.005 | | | 1 | |
| 0.01 | | | 3 | |
| 0.025 | | | 8 | |
| 0.05 | | | 18 | |
| | 0.05 | | 1 | |
| | 0.1 | | 8 | |
| 0.005 | 0.05 | 1:10 | 16 | 2 |
| 0.01 | 0.05 | 1:5 | 16 | 4 |
| | 0.1 | 1:10 | 32 | 11 |
| 0.025 | 0.05 | 1:2 | 31 | 9 |
| | 0.1 | 1:4 | 41 | 15 |
| | 0.25 | 1:10 | 13 | 23 |
| 0.05 | 0.05 | 1:1 | 26 | 19 |

B-4

Activity against *Puccinia recondita* in wheat

Curative action

Wheat plants, cv. Arina are grown in standard soil in 4 cm square pots (approx. 15 plants per pot) in a climatic chamber at 18° C. and a photo period of 12 hours per day. At test begin the plants are 7 days old. A suspension of 80'000 conidia /ml (0.1% Tween 20) of *Puccinia recondita*, is prepared from heavily sporulating cultures and sprayed on the test plants. The inoculated wheat plants are incubated in the green house for 24 hours under a plastic cover at 18–20° C. and 100% rH with reduced light. Then they are incubated for further 7 days in the greenhouse at 18–20° C. and 60% rH and a photoperiod of 14 hours. After 48 hours the test plants were removed from the green house for treatment for the curative applications and returned back immediately there after. The active ingredients are suspended in water and diluted to the intended concentrations shortly prior to the application. For each application two replicates were made. The percentage of activity is estimated, relative to the disease attack on the inoculated check plants. The fungicide interactions in the mixtures are calculated according to the COLBY method.

Results:

a) Mixtures of Compound 1.07 with Cyproconazole, *P. recondita*, curative

| Comp. 1.07 (mg a.i./l) | Cyproconazole (mg a.i./l) | Mixing ratio | % activity observed | % activity expected |
|---|---|---|---|---|
| 0.01 | | | 0 | |
| 0.025 | | | 0 | |
| 0.05 | | | 0 | |
| 0.1 | | | 0 | |
| 0.25 | | | 0 | |
| 0.5 | | | 0 | |
| 1 | | | 0 | |
| | 0.05 | | 15 | |
| | 0.1 | | 5 | |
| | 0.25 | | 65 | |
| | 0.5 | | 90 | |
| | 1 | | 85 | |
| | 2.5 | | 98 | |
| | 5 | | 95 | |
| | 10 | | 100 | |
| 0.01 | 0.05 | 1:5 | 85 | 15 |
| | 0.1 | 1:10 | 90 | 5 |
| 0.025 | 0.05 | 1:2 | 90 | 15 |
| | 0.1 | 1:4 | 85 | 5 |
| | 0.25 | 1:10 | 90 | 65 |
| 0.05 | 0.05 | 1:1 | 80 | 15 |
| | 0.1 | 1:2 | 70 | 5 |
| | 0.25 | 1:5 | 90 | 65 |
| | 0.5 | 1:10 | 95 | 90 |
| 0.1 | 0.05 | 2:1 | 80 | 15 |
| | 0.1 | 1:1 | 75 | 5 |
| | 0.5 | 1:5 | 98 | 90 |
| | 1 | 1:10 | 98 | 85 |
| 0.25 | 0.05 | 5:1 | 0 | 15 |
| | 0.25 | 1:1 | 85 | 65 |
| | 0.5 | 1:2 | 90 | 90 |
| | 1 | 1:4 | 98 | 85 |
| | 2.5 | 1:10 | 95 | 98 |
| 0.5 | 0.1 | 5:1 | 85 | 5 |
| | 0.25 | 2:1 | 80 | 65 |
| | 0.5 | 1:1 | 90 | 90 |
| | 1 | 1:2 | 98 | 85 |
| | 2.5 | 1:5 | 100 | 98 |
| | 5 | 1:10 | 98 | 95 |
| 1 | 0.25 | 4:1 | 95 | 65 |
| | 0.5 | 2:1 | 95 | 90 |
| | 1 | 1:1 | 98 | 85 |
| | 5 | 1:5 | 100 | 95 |
| | 10 | 1:10 | 95 | 100 | b) Mixtures of Compound 1.07 with Fenpropidin, *P. recondita*, curative

| Comp 1.07 (mg a.i./l) | Fenpropidine (mg a.i./l) | Mixing ratio | % activity observed | % activity expected |
|---|---|---|---|---|
| 5 | | | 35 | |
| | 1 | | 0 | |
| | 2.5 | | 0 | |

-continued

| Comp 1.07 (mg a.i./l) | Fenpropidine (mg a.i./l) | Mixing ratio | % activity observed | % activity expected |
|---|---|---|---|---|
| | 5 | | 0 | |
| | 10 | | 0 | |
| 5 | 25 | | 0 | |
| | 1 | 5:1 | 75 | 35 |
| | 2.5 | 2:1 | 60 | 35 |
| | 5 | 1:1 | 55 | 35 |
| | 10 | 1:2 | 35 | 35 |
| | 25 | 1:5 | 45 | 35 | c) Mixtures of Compound 1.07 with Propiconazole, *P. recondita*, curative

| Comp. 1.07 (mg a.i./l) | Propiconazole (mg a.i./l) | Mixing ratio | % activity observed | % activity expected |
|---|---|---|---|---|
| 0.25 | | | 0 | |
| 0.5 | | | 0 | |
| 1 | | | 0 | |
| 2.5 | | | 30 | |
| 5 | | | 35 | |
| | 1 | | 0 | |
| | 2.5 | | 20 | |
| 0.25 | 1 | 1:4 | 8 | 0 |
| | 2.5 | 1:10 | 25 | 20 |
| 0.5 | 1 | 1:2 | 0 | 0 |
| | 2.5 | 1:5 | 95 | 20 |
| 1 | 1 | 1:1 | 45 | 0 |
| 2.5 | 2.5 | 1:1 | 65 | 44 |
| 5 | 1 | 5:1 | 75 | 35 |
| | 2.5 | 2:1 | 85 | 48 | d) Mixtures of Compound 1.07 with Trifloxystrobin, *P. recondita*, curative

| Comp. 1.07 (mg a.i./l) | Trifloxystrobin (mg a.i./l) | Mixing ratio | % activity observed | % activity expected |
|---|---|---|---|---|
| 2.5 | | | 30 | |
| 5 | | | 35 | |
| | 1 | | 0 | |
| | 5 | | 0 | |
| | 10 | | 0 | |
| | 25 | | 35 | |
| | 50 | | 35 | |
| 2.5 | 5 | 1:2 | 50 | 30 |
| | 25 | 1:10 | 75 | 55 |
| 5 | 1 | 5:1 | 65 | 35 |
| | 5 | 1:1 | 70 | 35 |
| | 10 | 1:2 | 75 | 35 |
| | 25 | 1:5 | 75 | 58 |
| | 50 | 1:10 | 80 | 58 |

EXAMPLE B-5

Activity against *Phytophthora infestans* in tomatoes a) Curative action

Tomato plants cv. "Rotor Gnom" are grown for three weeks and then sprayed with a zoospore suspension of the fungus and incubated in a cabin at 18 to 20° C. and saturated atmospheric humidity. The humidification is interrupted after 24 hours. After the plants have dried, they are sprayed with a mixture which comprises the active ingredient formulated as a wettable powder at a concentration of 200 ppm. After the spray coating has dried, the plants are returned to the humid chamber for 4 days. Number and size of the typical foliar lesions which have appeared after this time are used as a scale for assessing the efficacy of the test substances.

b) Preventive-systemic action

The active ingredient which is formulated as a wettable powder is introduced, at a concentration of 60 ppm (relative to the soil volume), onto the soil surface of three-week-old tomato plants cv. "Rotor Gnom" in pots. After an interval of three days, the underside of the leaves is sprayed with a zoospore suspension of *Phytophthora infestans*. They are then kept for 5 days in a spray cabinet at 18 to 20° C. and saturated atmospheric humidity. After this time, typical foliar lesions appear whose number and size are used for assessing the efficacy of the test substances.

EXAMPLE B-6

Activity against *Septoria nodorum* in wheat a) Protective action

Wheat plants, cv. Arina are grown in standard soil in 6.5 cm round pots (approx. 8–10 plants per pot) in a climatic chamber at 18° C. and a photo period of 12 hours per day. At begin of the test the plants are 7 days old. The plants are sprayed with a spray mixture of the active ingredients prepared shortly before application. After 8 days, the treated plants are infected with a conidia suspension of *Septoria nodorum* (700'000 conidia /ml; 0.02% Tween 20) prepared from heavily sporulating cultures. The inoculated wheat plants are incubated in the green house for 24 hours under a dark nylon cover at 22–24° C. and 100% rH with reduced light. Then they are incubated for further 5 days in the greenhouse at 22–24° C. and 65% rH and a photoperiod of 14 hours. For each application two replicates are made. The percentage of activity is estimated, relative to the disease attack on the inoculated check plants. The fungicide interactions in the mixtures are calculated according to the COLBY method.

Results:

aa) Mixtures of Compound 1.07 with Cyproconazole, *S. nodorum*, preventive

| Comp. 1.07 (mg a.i./l) | Cyproconazole (mg a.i./l) | Mixing ratio | % activity observed | % activity expected |
|---|---|---|---|---|
| 0.1 | | | 0 | |
| 0.5 | | | 0 | |
| 1 | | | 0 | |
| 2.5 | | | 75 | |
| | 0.1 | | 0 | |
| | 0.5 | | 0 | |
| | 1 | | 0 | |
| | 5 | | 18 | |
| | 10 | | 35 | |
| | 25 | | 18 | |
| 0.1 | 0.1 | 1:1 | 35 | 0 |
| | 0.5 | 1:5 | 35 | 0 |
| | 1 | 1:10 | 50 | 0 |
| 0.5 | 0.1 | 5:1 | 65 | 0 |
| | 5 | 1:10 | 65 | 18 |
| 1 | 0.25 | 4:1 | 65 | 0 |
| | 5 | 1:5 | 65 | 18 |
| | 10 | 1:10 | 50 | 35 |
| 2.5 | 2.5 | 1:1 | 90 | 75 |
| | 5 | 1:2 | 95 | 79 |
| | 10 | 1:4 | 90 | 84 |
| | 25 | 1:10 | 98 | 79 | ab) Mixtures of Compound 1.07 with Cyprodinil, *S. nodorum*, preventive

| Comp. 1.07 (mg a.i./l) | Cyprodinil (mg a.i./l) | Mixing ratio | % activity observed | % activity expected |
|---|---|---|---|---|
| 0.01 | | | 0 | |
| 0.025 | | | 0 | |
| 0.1 | | | 0 | |
| 0.25 | | | 0 | |
| 0.5 | | | 0 | |
| 1 | | | 0 | |
| 2.5 | | | 75 | |
| | 0.1 | | 0 | |
| | 0.25 | | 0 | |
| | 0.5 | | 0 | |
| | 1 | | 0 | |
| | 2.5 | | 0 | |
| | 10 | | 0 | |
| 0.01 | 0.1 | 1:10 | 65 | 0 |
| 0.025 | 0.05 | 1:2 | 35 | 0 |
| | 0.1 | 1:4 | 18 | 0 |
| 0.25 | 1 | 1:4 | 18 | 0 |
| 0.5 | 1 | 1:2 | 35 | 0 |
| | 2.5 | 1:5 | 0 | 0 |
| 1 | 0.25 | 4:1 | 75 | 0 |
| | 0.5 | 2:1 | 70 | 0 |
| | 10 | 1:10 | 65 | 0 |
| 2.5 | 0.5 | 5:1 | 90 | 75 |
| | 2.5 | 1:1 | 90 | 75 |
| | 10 | 1:4 | 95 | 75 | ac) Mixtures of Compound 1.07 with Fenpropidin, *S. nodorum*, preventive

| Comp. 1.07 (mg a.i./l) | Fenpropidin (mg a.i./l) | Mixing ratio | % activity observed | % activity expected |
|---|---|---|---|---|
| 0.25 | | | 0 | |
| 1 | | | 0 | |
| 2.5 | | | 75 | |
| | 0.05 | | 0 | |
| | 0.25 | | 0 | |
| | 0.5 | | 0 | |
| | 1 | | 18 | |
| | 2.5 | | 0 | |
| | 5 | | 0 | |
| | 10 | | 0 | |
| | 25 | | 0 | |
| 0.25 | 0.05 | 5:1 | 90 | 0 |
| | 0.25 | 1:1 | 90 | 0 |
| | 0.5 | 1:2 | 50 | 0 |
| | 1 | 1:4 | 50 | 18 |
| 1 | 0.25 | 4:1 | 50 | 0 |
| | 0.5 | 2:1 | 80 | 0 |
| | 1 | 1:1 | 75 | 18 |
| | 5 | 1:5 | 75 | 0 |
| | 10 | 1:10 | 75 | 0 |
| 2.5 | 0.5 | 5:1 | 90 | 75 |
| | 2.5 | 1:1 | 85 | 75 |
| | 5 | 1:2 | 80 | 75 |
| | 10 | 1:4 | 95 | 75 |
| | 25 | 1:10 | 98 | 75 | b) Curative action

Wheat plants, cv. Arina are grown in standard soil in 4 cm square pots (approx. 15 plants per pot) in a climatic chamber at 18° C. and a photo period of 12 hours per day. At test begin the plants are 7 days old. A suspension of 700'000 conidia /ml (0.02% Tween 20) of *Septoria nodorum*, is prepared from heavily sporulating cultures and sprayed on the test plants. The inoculated wheat plants are incubated in the green house for 24 hours under a dark nylon cover at 22–24° C. and 100% rH with reduced light. Then they are incubated for further 5 days in the greenhouse at 22–24° C. and 65% rH and a photoperiod of 14 hours. After 48 hours the test plants were removed from the green house for treatment for the curative applications and returned back immediately there after. The active ingredients are suspended in water and diluted to the intended concentrations shortly prior to the application. For each application two replicates are made. The percentage of activity is estimated, relative to the disease attack on the inoculated check plants. The fungicide interactions in the mixtures are calculated according to the COLBY method.

Results:

ba) Mixtures of Compound 1.07 with Fenpropidin, *S. nodorum*, curative

| Comp. 1.07 (mg a.i./l) | Fenpropidin (mg a.i./l) | Mixing ratio | % activity observed | % activity expected |
|---|---|---|---|---|
| 0.01 | | | 0 | |
| 0.025 | | | 25 | |
| 0.05 | | | 20 | |
| | 0.1 | | 0 | |
| | 0.25 | | 0 | |
| | 0.5 | | 0 | |
| 0.01 | 0.1 | 1:10 | 35 | 0 |
| 0.025 | 0.1 | 1:4 | 90 | 25 |
| | 0.25 | 1:10 | 75 | 25 |
| 0.05 | 0.1 | 1:2 | 80 | 20 |
| | 0.25 | 1:5 | 55 | 20 |
| | 0.5 | 1:10 | 70 | 20 | bb) Mixtures of Compound 1.07 with Trifloxystrobin, *S. nodorum*, curative

| Comp. 1.07 (mg a.i./l) | Trifloxystrobin (mg a.i./l) | Mixing ratio | % activity observed | % activity expected |
|---|---|---|---|---|
| 0.01 | | | 0 | |
| 0.025 | | | 25 | |
| 0.05 | | | 20 | |
| | 0.05 | | 0 | |
| | 0.1 | | 0 | |
| | 0.25 | | 18 | |
| 0.01 | 0.05 | 1:5 | 70 | 0 |
| | 0.1 | 1:10 | 75 | 0 |
| 0.025 | 0.05 | 1:2 | 80 | 25 |
| | 0.1 | 1:4 | 35 | 25 |
| 0.05 | 0.05 | 1:1 | 90 | 20 |
| | 0.1 | 1:2 | 95 | 20 |
| | 0.25 | 1:5 | 65 | 34 |
| | 0.5 | 1:10 | 65 | 60 |

EXAMPLE B-7

Activity against Phytophthora in potato plants a) Residual-protective action

2–3 week old potato plants (Bintje variety) are grown for 3 weeks and then sprayed with a spray mixture (0.02% of active ingredient) prepared with a wettable powder of the active ingredient. After 24 hours, the treated plants are infected with a sporangia suspension of the fungus. The fungus infestation is assessed after the infected plants have been incubated for 5 days at a relative atmospheric humidity of 90–100% and 20° C.

b) Systemic action

A spray mixture (0.002% of active ingredient based on the soil volume) prepared with a wettable powder of the active ingredient is poured next to 2–3 week old potato plants (Bintje variety) which have been grown for 3 weeks. Care is taken that the spray mixture does not come into contact with the aerial parts of the plants. After 48 hours, the treated plants are infected with a sporangia suspension of the fungus. Fungus infestation is assessed after the infected plants have been incubated for 5 days at a relative atmospheric humidity of 90–100% and 20° C.

EXAMPLE B-8

Activity against *Phytophthora infestans* in potatoes

Potatoes, cv. Bintje are cultivated under greenhouse conditions at 24/20° C. in standard soil for 6 weeks. Leaf discs with a diameter of 10 mm are cut out of the leaves with the exception of the youngest and the oldest leaf. The leaf segments are placed with the upper leaf side down in petri dishes (ø 5 cm), each containing 6 ml of 0.16% water agar. The fungicides and mixtures are suspended in demineralized water and diluted appropriately. The fungicide treatment is carried out 1 day prior to inoculation. A total volume of 450 µl is applied on 6 leaf discs with an air brush. Freshly formed sporangia of *Phytophthora infestans* are harvested from infected potato slices and a sporangia suspension of 20'000 sporangia/ml is prepared; the suspension is incubated at 4° C. for 15 min.. For inoculation, a drop of 30 µl is applied to each leaf disc. The leaf discs are incubated for 6 d at 18° C. and a light period of 16 h until evaluation.

Six discs per treatment are evaluated. After the incubation period, the percentage of leaf attack is estimated and the activity is calculated relative to the check plants. The fungicide interactions in the mixtures are calculated according to the COLBY method.

Results:

Mixtures of Compound 1.07 with Trifloxystrobin

| Comp. 1.07 (mg a.i./l) | Trifloxystrobin (mg a.i./l) | Mixing ratio | % activity observed | % activity expected |
|---|---|---|---|---|
| 0.25 | | | 4 | |
| 0.1 | | | 0 | |
| | 2.5 | | 44 | |
| | 1 | | 6 | |
| | 0.5 | | 6 | |
| | 0.25 | | 0 | |
| | 0.1 | | 2 | |
| 0.25 | 2.5 | 1:10 | 67 | 46 |
| | 1 | 1:4 | 59 | 10 |
| | 0.5 | 1:2 | 9 | 9 |
| | 0.25 | 1:1 | 17 | 4 |
| 0.1 | 1 | 1:10 | 20 | 6 |
| | 0.5 | 1:5 | 19 | 6 |
| | 0.25 | 1:2.5 | 20 | 0 |
| | 0.1 | 1:1 | 15 | 2 |

EXAMPLE B-9

Activity against *Helminthosporium teres* on barley

Barley plants, cv. Express are grown in standard soil in 6.5 cm round pots (approx. 8–10 plants per pot) in a climatic chamber at 18° C. and at a photo period of 12 hours per day. At test begin the plants were 7 days old. The plants are sprayed with a spray mixture of the active ingredients prepared shortly before application. After 9 days, the treated plants are infected with a conidia suspension of *Helminthosporium teres* prepared from heavily sporulating cultures. A suspension of 30'000 conidia /ml (0.1% Tween 20) is prepared from the in-vitro cultures and sprayed immediately on the test plants. The inoculated barley plants are incubated in the green house for 3 days under a plastic cover at 20–22° C. and 100% rH and a photoperiod of 14 hours. For each application two repetitions are made. The efficacy of the test combinations and the single active ingredients in this test is determined by comparing the degree of fungal attack with that on untreated, similarly inoculated check plants. The percentage of activity is estimated, relative to the disease attack on the inoculated check plants. The fungicide interactions in the mixtures are calculated according to the COLBY method.

Results:

a) Mixtures of Compound 1.07 with Cyprodinil, *H. teres*, preventive

| Comp. 1.07 (mg a.i./l) | Cyprodinil (mg a.i./l) | Mixing ratio | % activity observed | % activity expected |
|---|---|---|---|---|
| 2.5 | | | 35 | |
| 5 | | | 50 | |
| 10 | | | 60 | |
| | 10 | | 0 | |
| | 25 | | 0 | |
| | 50 | | 0 | |
| | 100 | | 0 | |
| 2.5 | 10 | 1:4 | 60 | 35 |
| 5 | 10 | 1:2 | 65 | 50 |
| | 25 | 1:5 | 60 | 50 |
| | 50 | 1:10 | 65 | 50 |
| 10 | 50 | 1:5 | 70 | 60 |
| | 100 | 1:10 | 75 | 60 | b) Mixtures of Compound 1.07 with Fenpropidin, *H. teres*, preventive

| Comp. 1.07 (mg a.i./l) | Fenpropidin (mg a.i./l) | Mixing ratio | % activity observed | % activity expected |
|---|---|---|---|---|
| 1 | | | 0 | |
| 2.5 | | | 35 | |
| 5 | | | 50 | |
| 10 | | | 60 | |
| | 0.25 | | 0 | |
| | 0.5 | | 0 | |
| | 2.5 | | 0 | |
| | 5 | | 0 | |
| | 10 | | 0 | |
| | 25 | | 0 | |
| | 50 | | 0 | |
| | 100 | | 0 | |
| 1 | 0.25 | 4:1 | 25 | 0 |
| | 5 | 1:5 | 35 | 0 |
| | 10 | 1:10 | 20 | 0 |
| 2.5 | 0.5 | 5:1 | 45 | 35 |
| | 2.5 | 1:1 | 40 | 35 |
| | 10 | 1:4 | 50 | 35 |
| | 25 | 1:10 | 55 | 35 |
| 5 | 2.5 | 2:1 | 80 | 50 |
| | 5 | 1:1 | 50 | 50 |
| | 10 | 1:2 | 60 | 50 |
| | 25 | 1:5 | 55 | 50 |
| | 50 | 1:10 | 60 | 50 |
| 10 | 2.5 | 4:1 | 70 | 60 |
| | 5 | 2:1 | 70 | 60 |
| | 10 | 1:1 | 90 | 60 |
| | 50 | 1:5 | 80 | 60 |
| | 100 | 1:10 | 70 | 60 | c) Mixtures of Compound 1.07 with Propiconazole, *H. teres*, preventive

| Comp. 1.07 (mg a.i./l) | Propiconazole (mg a.i./l) | Mixing ratio | % activity observed | % activity expected |
|---|---|---|---|---|
| 5 | | | 50 | |
| 10 | | | 60 | |
| | 5 | | 0 | |
| | 10 | | 0 | |
| | 25 | | 0 | |
| | 50 | | 0 | |
| 5 | 5 | 1:1 | 55 | 50 |
| | 10 | 1:2 | 65 | 50 |
| | 25 | 1:5 | 70 | 50 |
| | 50 | 1:10 | 80 | 50 |
| 10 | 10 | 1:1 | 55 | 60 |
| | 50 | 1:5 | 75 | 60 |
| | 100 | 1:10 | 80 | 67 |

EXAMPLE B-10

Action against *Colletotrichum lagenarium* on *Cucumis sativus* a) After a cultivation period of 1 weeks, cucumber plants are sprayed with a spray mixture prepared from a wettable powder formulation of the test compounds (three concentrations each). After 96 hours, the plants are infected with a spore suspension ($1.0 \times 10^5$ spores/ml) of the fungus and incubated for 30 hours at high humidity and a temperature of 20° C. Incubation is then continued at normal humidity and 22° C. to 23° C.

Evaluation of protective action is made 7 to 8 days after infection and is based on fungus infestation, relative to untreated check plants. The evaluation of the interaction of the two active ingredient components is calculated according to the COLBY method.

Results:

Mixtures of Compound 1.07 with Acibenzolar-S-methyl

| Comp. 1.07 (mg a.i./l) | Acibenzolar-S-methyl (mg a.i./l) | Mixing ratio | % activity observed | % activity expected |
|---|---|---|---|---|
| 0.06 | | | 0 | |
| 0.2 | | | 0 | |
| 0.6 | | | 0 | |
| | 0.06 | | 0 | |
| | 0.2 | | 0 | |
| | 0.6 | | 0 | |
| 0.06 | 0.06 | 1:1 | 38 | 0 |
| | 0.2 | 1:3 | 75 | 0 |
| | 0.6 | 1:10 | 94 | 0 |
| 0.2 | 0.06 | 3:1 | 88 | 0 |
| | 0.2 | 1:1 | 69 | 0 |
| | 0.6 | 1:3 | 88 | 0 |
| 0.6 | 0.06 | 10:1 | 93 | 0 |
| | 0.2 | 3:1 | 89 | 0 |
| | 0.6 | 1:1 | 94 | 0 | b) After a cultivation period of 2 weeks, cucumber plants are treated by soil application with a spray mixture prepared from a wettable powder formulation of the test compound (concentration: 60 ppm, based on the volume of the soil). After 96 hours, the plants are infected with a spore suspension ($1.5 \times 10^5$ spores/ml) of the fungus and incubated for 30 hours at high humidity and a temperature of 20° C. Incubation is then continued at normal humidity and 22° C.

Evaluation of protective action is made 7 to 8 days after infection and is based on fungus infestation.

The mixtures according to the invention exhibit good activity in the above Examples.

What is claimed is:

1. A method of combating phytopathogenic diseases on crop plants which comprises applying to the crop plants or the locus thereof being infested with said phytopathogenic disease an effective amount of a combination of a) a 2-(5-phenyl-3,6-diaza-2,7-dioxa-octa-3,5-dienyl)-phenylacrylamide of formula I

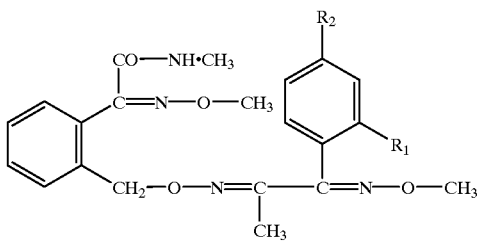

wherein $R_1$ is hydrogen, fluoro or chloro, $R_2$ is methyl, ethyl, trifluoromethyl, trifluoromethoxy, cyano, fluoro, chloro or bromo, with the proviso that $R_2$ cannot be fluoro, chloro or bromo, when $R_1$ is hydrogen;

in association with b) either an anilinopyrimidine of formula II

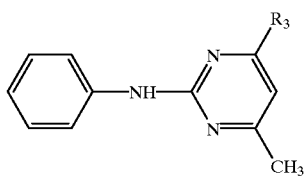

wherein $R_3$ is methyl, 1-propynyl or cyclopropyl;

or an azole of formula III

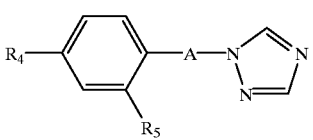

wherein

A is selected from

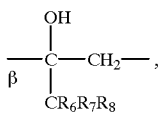

(ii) [structure: β-O-C(-CH₂-)-O-CH₂ with CR₆R₇R₈]

(iii) [structure: β-CH₂-CH₂-C(OH)(CR₆R₇R₈)-CH₂-]

(iv) [structure: β-cyclopentane with =CH-OH, CH₂-, R₆, R₇]

(v) [structure: β-C(OH)(R₉)-CH₂-]

(vi) [structure: β-CH(epoxide)-C(R₉)-CH₂-]

(vii) [structure: β-CH₂-C(CN)(R₁₀)-CH₂-]

(viii) [structure: β-tetrahydrofuran with CH₂- and Br]

(ix) [structure: β-CH(R₁₁)-CH₂-]

(x) [structure: β-Si(R₈)(R₉)-CH₂-]

(xi) [structure: β-cyclopentane with CH₂, OH, CH₂-, R₆, R₇]

(xii) [structure: β-CH=C(CR₆R₇R₈)-]

(xiii) [structure: β-fluoro-quinazolinone with N-CH₃ and =N-CH₃]

(xiv) [structure: β-C(CN)(CR₆R₇R₈)-CH₂- and,]

(xv) [structure: β-O-CH(-CH(OH)-CR₆R₇R₈)-] ;

whereby the β-carbon attaches to benzene ring of formula III, and wherein $R_4$ is H, F, Cl, 4-fluorophenoxy or 4-chlorophenoxy;
$R_5$ is H, Cl or F;
$R_6$ and $R_7$ are independently H or CH₃;
$R_8$ is $C_{1-4}$alkyl or cyclopropyl;
$R_9$ is 4-chlorophenyl or 4-fluorophenyl;
$R_{10}$ is phenyl, and
$R_{11}$ is allyloxy, $C_{1-4}$alkyl, or 1,1,2,2-tetrafluoroethoxymethyl, and the salts of such azole fungicide;
or a morpholine fungicide of formula IV (IV) [structure: morpholine with 2,6-dimethyl and N-R₁₂]

wherein $R_{12}$ is $C_{8-15}$cycloalkyl, $C_{8-15}$alkyl, or $C_{1-4}$alkylphenyl-$C_{1-4}$alkyl, and the salts of such morpholine fungicide;
or a strobilurin compound of formula V (V) [structure: phenyl with =Y-O-CH₃ and CO-X-CH₃ substituents and R₁₃ ortho]

wherein

X is NH or O,
Y is CH or N, and
$R_{13}$ is 2-methylphenoxy-methyl, 2,5-dimethylphenoxy-methyl, 4-(2-cyanophenoxy)-pyrimidin-6-yloxy, or 4-(3-trifluoromethylphenyl)-3-aza-2-oxa-4-pentenyl;

or a pyrrole compound of the formula VI (VI)

wherein

R$_{14}$ and R$_{15}$ are indendently halo, or together from a perhalomethylendioxo bridge;

or a phenylamide of the formula VII (VII)

wherein

R$_{16}$ is benzyl, methoxymethyl, 2-furanyl or chloromethyl,

R$_{17}$ is 1-methoxycarbonyl-ethyl, or

Z is CH or N;

or a dithiocarbamate fungicide selected from mancozeb, maneb, metiram and zineb;

or a copper compound selected from copper hydroxide, copper oxychloride, copper sulfate and oxine-copper;

or sulfur;

or a phthalimide compound of the formula VIII (VIII)

wherein

R$_{18}$ and R$_{19}$ together form a 4-membered bridge —CH$_2$—CH=CH—CH$_2$— or =CH—CH=CH—CH=;

or with the compound of formula IX (IX)

or with the compound of formula X (X)

or with the compound of formula XI (XI)

or with the compound of formula XII (XII)

or with the compound of formula XIII (XIII)

or with the compound of formula XIV (XIV)

H$_3$C—CH$_2$—NH—C(=O)—NH—C(=O)—C(CN)=N—OCH$_3$;

or with the compound of formula XV (XV)

or with the compound of formula XVI (XVI)

or with the compound of formula XVII (XVII)

or with the compound of formula XVIII (XVIII)

or with the compound of formula XIX (XIX)

or with the compound of formula XX (XX)

or with the compound of formula XXI (XXI)

or with the compound of formula XXII (XXII)

or with the compound of formula XXIII (XXIII)

or with the compound of formula XXIV (XXIV)

or with 2-chloro- N-(4'-fluoro-1,1'-biphenyl-2-yl) nicotinamide (compound XXV),
or with 2-chloro- N-(4'-chloro-1,1'-biphenyl-2-yl) nicotinamide (compound XXVI),
or with methyl N-(2-[1-(4-chlorophenyl)pyrazol-3-yloxymethyl]phenyl)-N-methoxycarbamate (compound XXVII),
or with methyl N-(2-[1-(4-tolyl)pyrazol-3-yloxymethyl] phenyl)-N- methoxycarbamate (compound XXVIII),
or with 2-[4-methoxy-3-(1-methylethoxy)-1,4-diazabuta-1, 3-dienyloxymethyl]phenyl-2-methoximino-N-methylacetamide (compound XXIX),
or with 2-[4-methoxy-3-(1-methylpropoxy)-1,4-diazabuta-1,3-dienyloxymethyl]phenyl-2-methoximino-N-methylacetamide (compound XXX),
or with N-(cyclopropylmethoxy)-N'-(2-phenylacetyl)-2,3-difluoro-6-trifluoromethyl-benzamidine (compound XXXI), or with N-[3'-(1'-chloro-3-methyl 2'-oxopentan)]-3,5-dichloro-4-methylbenzamide (compound XXXII), or with methyl(2)-2-{6-[6-(trifluoromethyl)pyrid-2-yloxymethyl]-phenyl}-3-methoxyacrylate (compound XXXIII), or with 2-chloro-4-(2-fluoro-2-methylpropionylamino)-N,N-dimethylbenzamide (compound XXXIV), or with (S)-1-anilino-4-methyl-2-methylthio-4-phenylimidazolin-5-one (compound XXXV), or with N-methyl-2-{2-[α-methyl-3-(trifluoromethyl)benzyloximinomethyl]phenyl}-2-methoximinoacetamide (compound XXXVI), or with a (S)-valinamide of formula XXXVII)

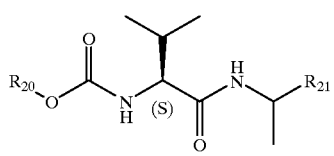

(XXXVII)

wherein $R_{20}$ is isopropyl, sec.-butyl or tert.-butyl, and $R_{21}$ is 4-chlorophenyl, 4-tolyl, 4-methoxyphenyl or β-naphthyl, or with a (S)-valinamide of formula XXXVIII

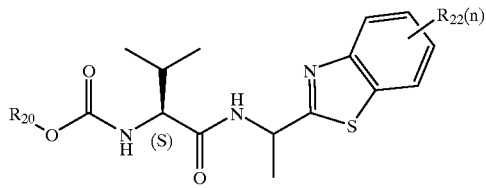

(XXXVIII)

wherein $R_{20}$ is isopropyl, sec.-butyl or tert.-butyl, $R_{22}$ is halogen, methyl or methoxy, and n is 0, 1, or 2;

or with an azole of formula XXXIX

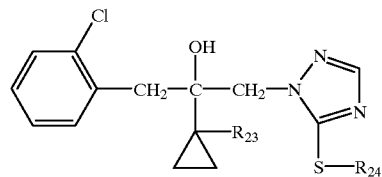

(XXXIX)

wherein $R_{23}$ is chloro or fluoro, and $R_{24}$ is hydrogen or methyl.

2. A method according to claim 1 wherein component b) does not comprise the compounds of formulae XXV to XXXVIII.

3. A method according to claim 1 wherein the component a) comprises a compound of the formula I wherein $R_1$ is fluoro or chloro and $R_2$ is methyl, trifluoromethyl, fluoro, chloro or bromo, or wherein $R_1$ is fluoro or chloro and $R_2$ is methyl, chloro or fluoro, or wherein $R_1$ and $R_2$ are independently fluoro or chloro, or wherein $R_1$ is hydrogen, fluoro or chloro and $R_2$ is methyl, fluoro or chloro, provided that $R_2$ is methyl when $R_1$ is hydrogen.

4. A method according to claim 1 wherein the component b) is selected from the group comprising pyrimethanil, cyprodinil, cyproconazole, hexaconazole; difenoconazole, etaconazole, propiconazole, tebuconazole, triticonazole, flutriafol, epoxiconazole, fenbuconazole, bromuconazole, penconazole, imazalil, tetraconazole, flusilazole, metconazole, diniconazole, fluquinconazole, myclobutanil, triadimenol, dodemorph, tridemorph, fenpropimorph, mancozeb, maneb, metiram, zineb, copper hydroxide, copper oxychloride, copper sulfate, oxine-copper, sulfur, kresoxim-methyl, azoxystrobin, 2-[2-(2,5-dimethoxyphenoxy-methyl)-phenyl]-2-methoximino-acetic acid N-methyl-amide, methyl 2-{2-[4-(3-trifluoromethylphenyl)-3-aza-2-oxa-4-pentenyl]-phenyl}-2-methoxyimino-acetate, fenpiclonil, fludioxonil, benalaxyl, furalaxyl, metalaxyl, R-metalaxyl, orfurace, oxadixyl, captan, folpet, prochloraz, triflumizole, pyrifenox, acibenzolar-S-methyl, chlorothalonil, cymoxanil, dimethomorph, famoxadone, fenhexamide, fenarimol, fluazinam, fosetyl-aluminium, quinoxyfen, fenpropidine, spiroxamine, and carbendazime.

5. A method according to claim 1 wherein the component b) is fenamidone or iprovalicarb.

6. A method according to claim 4 wherein component b) is selected from a group comprising cyproconazole, hexaconazole; difenoconazole, propiconazole, tebuconazole, flutriafol, epoxiconazole, fenbuconazole, bromuconazole, penconazole, tetraconazole, flusilazole, metconazole, diniconazole, triadimenol, fluquinconazole and prochloraz.

7. A method according to claim 4 wherein component b) is selected from a group comprising cyprodinil, tridemorph, fenpropimorph, kresoxim-methyl, azoxystrobin, methyl 2-{2-[4-(3-trifluoromethylphenyl)-3-aza-2-oxa-4-pentenyl]-phenyl}-2-methoxyimino-acetate, acibenzolar-S-methyl, chlorothalonil, famoxadone, quinoxyfen, fenpropidine and carbendazime.

8. A method according to claims 4, 6 or 7 wherein component a) is selected from the group consisting of a 2-(5-phenyl-3,6-diaza-2,7-dioxa-octa3,5-dienyl)-phenylacrylamide compound of formula I

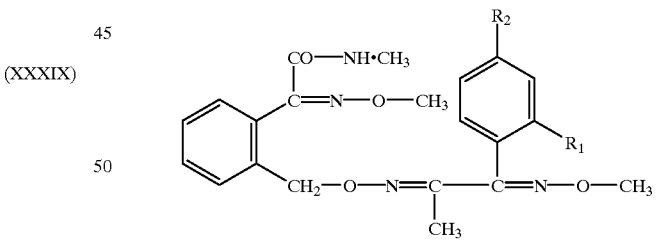

(I)

wherein $R_1$ is hydrogen and $R_2$ is 4-CH$_3$ (1.03), $R_1$ is 2-Cl and $R_2$ is 4-Cl (1.03), $R_1$ is hydrogen and $R_2$ is 4-OCF$_3$, $R_1$ is 2-F and $R_2$ is 4-CH3, $R_1$ is 2-F and $R_2$ is 4-F, $R_1$ is 2-Cl and $R_2$ is 4-F and $R_1$ is 2-F and $R_2$ is 4-Cl.

9. A method according to claim 1 wherein component b) is the compound isopropyl 2-methyl-1-[(1-p-tolylethyl) carbamoyl]-(S)-propylcarbamate (compound XXXVIIa).

10. A method according to claim 4 wherein component b) is selected from the group consisting of cyprodinil, fenpropimorph, kresoxim-methyl, azoxystrobin, methyl 2-{2-[4-(3-trifluoromethylphenyl)-3-aza-2-oxa-4-pentenyl]-phenyl}-2-methoxyimino-acetate, acibenzolar-S-methyl and fenpropidine.

11. A method according to claim 6 wherein component b) is selected from the group consisting of propiconazole, difenoconazole, penconazole, tebuconazole, prochloraz, epoxiconazole and cyproconazole.

12. A fungicidal composition comprising a fungicidally effective combination of the components
a) a 2-(5-phenyl-3,6-diaza-2,7-dioxa-octa-3,5dienyl)-phenylacrylamide of formula I

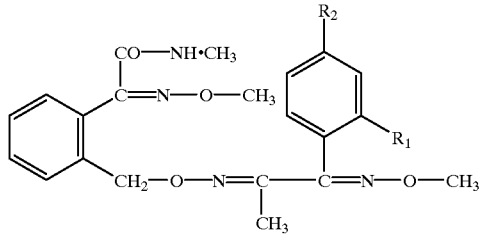
(I)

wherein
$R_1$ is hydrogen, fluoro or chloro,
$R_2$ is methyl, ethyl, trifluoromethyl, trifluoromethoxy, cyano, fluoro, chloro or bromo, with the proviso that $R_2$ cannot be fluoro, chloro or bromo, when $R_1$ is hydrogen; and
b) either an anilinopyrimidine of formula II

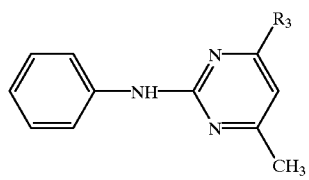
(II)

wherein
$R_3$ is methyl, 1-propynyl or cyclopropyl;
or an azole of formula III

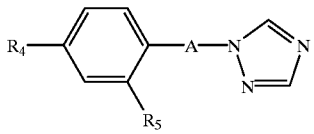
(III)

wherein
A is selected from

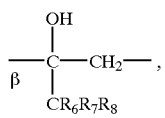
(i)

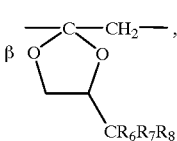
(ii)

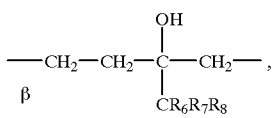
(iii)

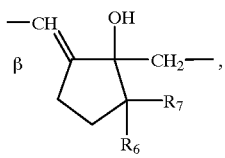
(iv)

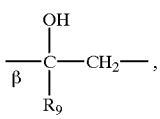
(v)

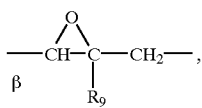
(vi)

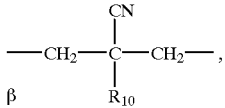
(vii)

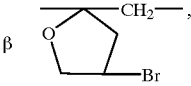
(viii)

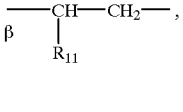
(ix)

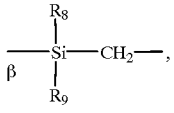
(x)

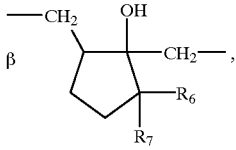
(xi)

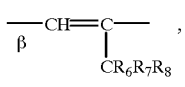
(xii)

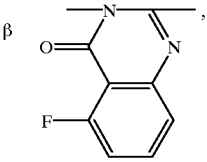
(xiii)

-continued (xiv)
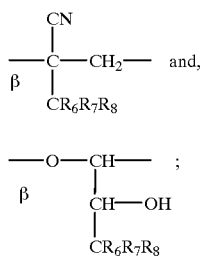 and, (xv)
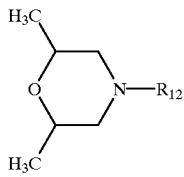

whereby the β-carbon attaches to benzene ring of formula III, and wherein
$R_4$ is H, F, Cl, 4-fluorophenoxy or 4-chlorophenoxy;
$R_5$ is H, Cl or F;
$R_6$ and $R_7$ are independently H or $CH_3$;
$R_8$ is $C_{1-4}$alkyl or cyclopropyl;
$R_9$ is 4-chlorophenyl or 4-fluorophenyl;
$R_{10}$ is phenyl, and
$R_{11}$ is allyloxy, $C_{1-4}$alkyl, or 1,1,2,2-tetrafluoroethoxy-methyl, and the salts of such azole fungicide;
or a morpholine fungicide of formula IV (IV)
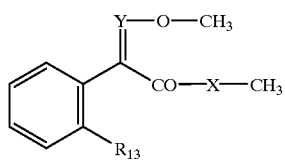

wherein
$R_{12}$ is $C_{8-15}$cycloalkyl, $C_{8-15}$alkyl, or $C_{1-4}$alkylphenyl-$C_{1-4}$alkyl, and the salts of such morpholine fungicide;
or a strobilurin compound of formula V (V)
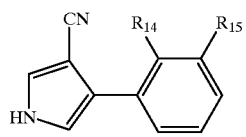

wherein
X is NH or O,
Y is CH or N, and
$R_{13}$ is 2-methylphenoxy-methyl, 2,5-dimethylphenoxy-methyl, 4-(2-cyanophenoxy)-pyrimidin-6-yloxy, or 4-(3-trifluoromethylphenyl)-3-aza-2-oxa-4pentenyl;
or a pyrrole compound of the formula VI (VI)

wherein
$R_{14}$ and $R_{15}$ are indentently halo, or together from a perhalomethylendioxo bridge;

or a phenylamide of the formula VII (VII)
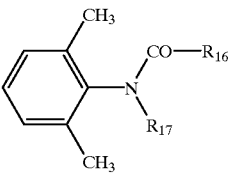

wherein
$R_{16}$ is benzyl, methoxymethyl, 2-furanyl or chloromethyl,
$R_{17}$ is 1-methoxycarbonyl-ethyl, or

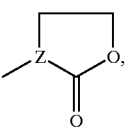

Z is CH or N;
or a dithiocarbamate fungicide selected from mancozeb, maneb, metiram and zineb;
or a copper compound selected from copper hydroxide, copper oxychloride, copper sulfate and oxine-copper;
or sulfur;
or a phthalimide compound of the formula VIII (VIII)
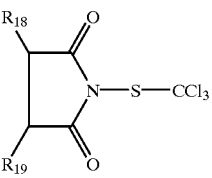

wherein
$R_{18}$ and $R_{19}$ together form a 4-membered bridge —$CH_2$—CH=CH—$CH_2$— or =CH—CH=CH—CH=;
or with the compound of formula IX (IX)
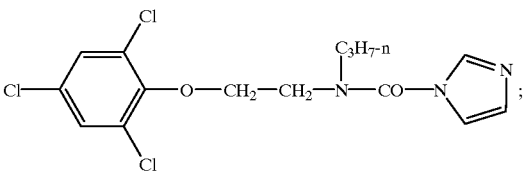

or with the compound of formula X (X)
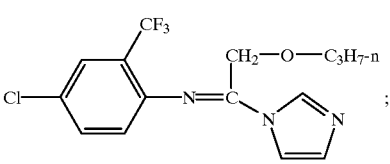

or with the compound of formula XI

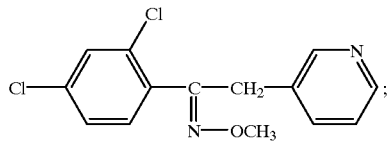
(XI)

or with the compound of formula XII

(XII)

or with the compound of formula XIII

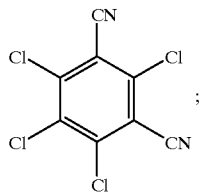
(XIII)

or with the compound of formula XIV

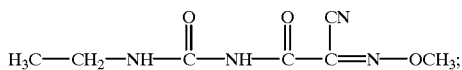
(XIV)

or with the compound of formula XV

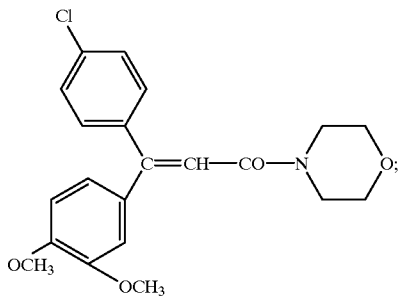
(XV)

or with the compound of formula XVI

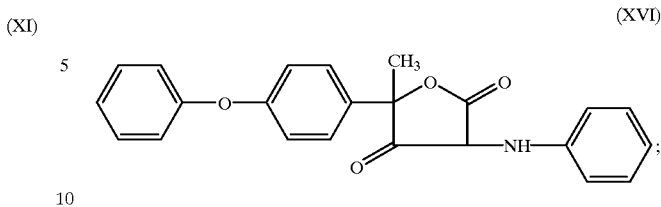
(XVI)

or with the compound of formula XVII

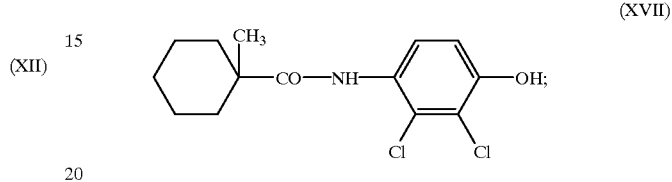
(XVII)

or with the compound of formula XVIII

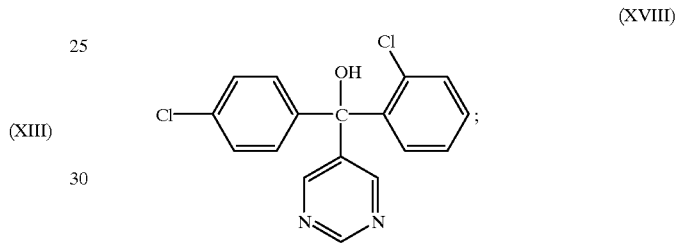
(XVIII)

or with the compound of formula XIX

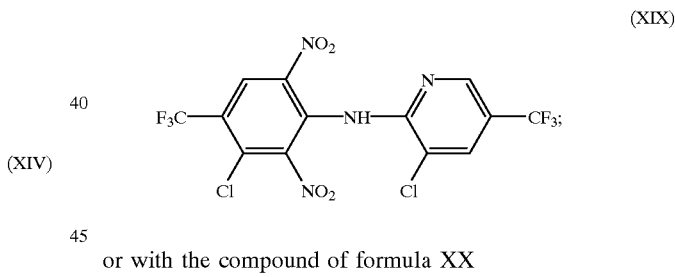
(XIX)

or with the compound of formula XX

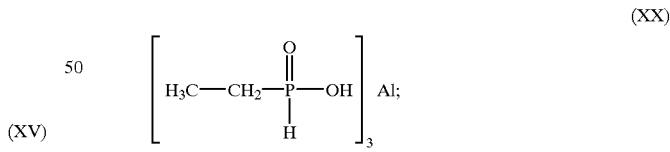
(XX)

or with the compound of formula XXI

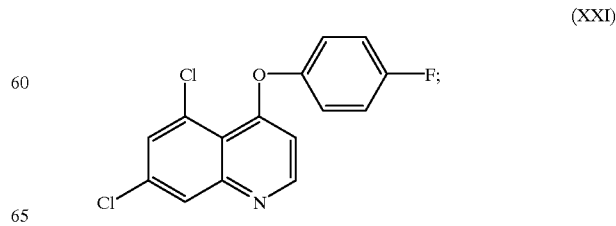
(XXI)

or with the compound of formula XXII (XXII)
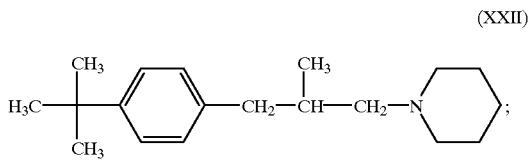

or with the compound of formula XXIII (XXIII)
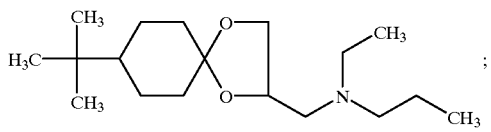

or with the compound of formula XXIV (XXIV)
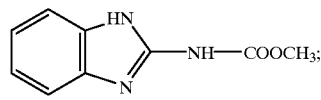

or with 2-chloro- N-(4'-fluoro-1,1'-biphenyl-2-yl) nicotinamide (compound XXV),
or with 2-chloro- N-(4'-chloro-1,1'-biphenyl-2-yl) nicotinamide (compound XXVI),
or with methyl N-(2-[1-(4-chlorophenyl)pyrazol-3-yloxymethyl]phenyl)-N-methoxycarbamate (compound XXVII),
or with methyl N-(2-[1-(4-tolyl)pyrazol-3-yloxymethyl] phenyl)-N-methoxycarbamate (compound XXVIII),
or with 2-[4-methoxy-3-(1-methylethoxy)-1,4-diazabuta-1,3-dienyloxymethyl]phenyl-2-methoximino-N-methylacetamide (compound XXIX),
or with 2-[4-methoxy-3-(1-methylpropoxy)-1,4-diazabuta-1,3-dienyloxymethyl]phenyl-2-methoximino-N-methylacetamide (compound XXX),
or with N-(cyclopropylmethoxy)-N'-(2-phenylacetyl)-2,3-difluoro-6-trifluoromethyl-benzamidine (compound XXXI),
or with N-[3'-(1'-chloro-3-methyl 2'-oxopentan)]-3,5-dichloro4-methylbenzamide (compound XXXII),
or with methyl(2)-2-{6-[6-(trifluoromethyl)pyrid-2-yloxymethyl]-phenyl}-3-methoxyacrylate (compound XXXIII),
or with 2-chloro-4(2-fluoro-2-methylpropionylamino)-N,N-dimethylbenzamide (compound XXXIV),
or with (S)-1-anilino-4-methyl-2-methylthio-4-phenylimidazolin-5-one (compound XXXV),
or with N-methyl-2-{2-[α-methyl-3-(trifluoromethyl) benzyloximinomethyl]phenyl}2-methoximinoacetamide (compound XXXVI), or with a (S)-valinamide of formula XXXVII)

(XXXVII)
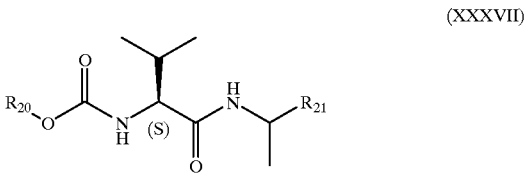

wherein
$R_{20}$ is isopropyl, sec.-butyl or tert.-butyl, and
$R_{21}$ is 4-chlorophenyl, 4-tolyl, 4-methoxyphenyl or β-naphthyl
or with a (S)-valinamide of formula XXXVIII (XXXVIII)
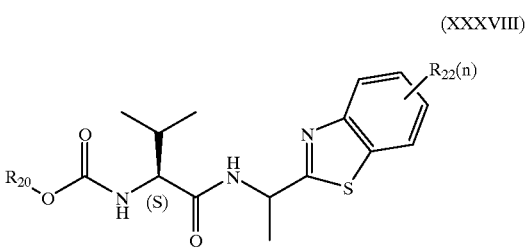

wherein
$R_{20}$ is isopropyl, sec.-butyl or tert.-butyl,
$R_{22}$ is halogen, methyl or methoxy, and n is 0, 1, or, 2;
or with an azole of formula XXXIX (XXXIX)
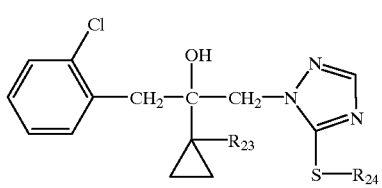

wherein
$R_{23}$ is chloro or fluoro, and
$R_{24}$ is hydrogen or methyl;
together with an agriculturally acceptable carrier, and optionally a surfactant.

13. A composition according to claim 12 wherein the weight ratio of a) to b) is between 10:1 and 1:400.

14. A fungicidal composition according to claim 12 wherein component b) is the compound isopropyl 2-methyl-1-[(1-p-tolylethyl)carbamoyl]-(S)-propylcarbamate (compound XXXVIIa).

* * * * *